United States Patent
Willemsen et al.

(10) Patent No.: US 11,098,115 B2
(45) Date of Patent: Aug. 24, 2021

(54) MULTI-SPECIFIC BINDING MOLECULES TARGETING ABERRANT CELLS

(71) Applicant: APO-T B.V., Amersfoort (NL)

(72) Inventors: Ralph Alexander Willemsen, Rotterdam (NL); Johan Renes, Amersfoort (NL)

(73) Assignee: APO-T B.V., Amersfoort (NL)

( * ) Notice: Subject to any disclaimer, the term of this patent is extended or adjusted under 35 U.S.C. 154(b) by 0 days.

(21) Appl. No.: 14/348,465

(22) PCT Filed: Sep. 26, 2012

(86) PCT No.: PCT/NL2012/050675
§ 371 (c)(1),
(2) Date: Mar. 28, 2014

(87) PCT Pub. No.: WO2013/048243
PCT Pub. Date: Apr. 4, 2013

(65) Prior Publication Data
US 2014/0227273 A1 Aug. 14, 2014

Related U.S. Application Data

(60) Provisional application No. 61/540,920, filed on Sep. 29, 2011.

(51) Int. Cl.
| | | |
|---|---|---|
| C07K 16/28 | (2006.01) | |
| C07K 14/725 | (2006.01) | |
| C07K 16/30 | (2006.01) | |
| A61P 35/00 | (2006.01) | |

(52) U.S. Cl.
CPC .......... C07K 16/28 (2013.01); C07K 14/7051 (2013.01); C07K 16/2809 (2013.01); C07K 16/30 (2013.01); A61P 35/00 (2018.01); C07K 2317/30 (2013.01); C07K 2317/31 (2013.01); C07K 2317/34 (2013.01); C07K 2317/569 (2013.01); C07K 2319/33 (2013.01)

(58) Field of Classification Search
CPC ................ C07K 16/28; C07K 14/7051; C07K 2317/622; C07K 16/2809; C07K 16/2896; C07K 16/30; C07K 2319/31; C07K 2319/32; C07K 2317/30; C07K 2319/33; C07K 2317/569; C07K 2317/31; C07K 2317/34; A61P 35/00; A61P 37/02
See application file for complete search history.

(56) References Cited

U.S. PATENT DOCUMENTS

| | | | |
|---|---|---|---|
| 5,709,995 A | 1/1998 | Chisari et al. | |
| 6,737,056 B1* | 5/2004 | Presta | C07K 16/28 424/133.1 |
| 7,488,793 B2* | 2/2009 | Van Der Bruggen | A61K 39/0011 530/326 |
| 7,635,472 B2* | 12/2009 | Kufer | C07K 16/2803 424/130.1 |
| 8,568,717 B2 | 10/2013 | De et al. | |
| 9,260,508 B2 | 2/2016 | Laeremans et al. | |
| 9,512,231 B2 | 12/2016 | Willemsen | |
| 9,821,073 B2 | 11/2017 | Willemsen et al. | |
| 10,946,104 B2 | 3/2021 | Renes et al. | |
| 2002/0155604 A1 | 10/2002 | Ledbetter et al. | |
| 2003/0223994 A1 | 12/2003 | Hoogenboom et al. | |
| 2004/0162411 A1* | 8/2004 | Lanzavecchia | C07K 16/2809 530/350 |
| 2004/0219643 A1 | 11/2004 | Winter et al. | |
| 2005/0026881 A1 | 2/2005 | Robinson et al. | |
| 2005/0037421 A1* | 2/2005 | Honda | C07K 16/00 435/7.1 |
| 2005/0084449 A1* | 4/2005 | Landes | C07K 16/28 424/1.49 |
| 2005/0136050 A1 | 6/2005 | Kufer et al. | |
| 2005/0175606 A1 | 8/2005 | Huang et al. | |
| 2005/0255101 A1 | 11/2005 | Reiter et al. | |
| 2005/0266425 A1* | 12/2005 | Zauderer | C07K 16/283 435/6.14 |
| 2005/0287141 A1 | 12/2005 | Reiter et al. | |
| 2006/0135418 A1 | 6/2006 | Jakobsen et al. | |
| 2006/0263381 A1 | 11/2006 | Kosmatopoulos et al. | |
| 2007/0140966 A1 | 6/2007 | Chang et al. | |
| 2008/0044413 A1* | 2/2008 | Hammond | C07K 16/2809 424/135.1 |

(Continued)

FOREIGN PATENT DOCUMENTS

| | | |
|---|---|---|
| GB | 0115841 | 2/1919 |
| GB | 0601513 | 5/1948 |

(Continued)

OTHER PUBLICATIONS

Rudikoff et al., Proc Natl Acad Sci USA vol. 79: 1979-1983, 1982.*
Wu et al., J. Mol. Biol. 294: 151-162, 1999.*
Stancovski et al., Proceedings of the National Academy of Science USA 88: 8691-8695, 1991.*
Schmidt et al., Britsh Journal of Cancer 74: 853-862,1996.*

(Continued)

*Primary Examiner* — Phuong Huynh

(74) *Attorney, Agent, or Firm* — TraskBritt

(57) ABSTRACT

Described are proteinaceous molecules comprising at least two, preferably three to six, binding domains that bind specifically to at least two different binding sites on aberrant cells. These multi-domain and multi-specific binding molecules are preferably used in selectively modulating biological processes. The provided binding molecules are of particular use in pharmaceutical compositions for the treatment of diseases related to cellular aberrancies, such as cancers and autoimmune diseases.

13 Claims, 4 Drawing Sheets

Specification includes a Sequence Listing.

(56) References Cited

U.S. PATENT DOCUMENTS

| | | | |
|---|---|---|---|
| 2008/0280346 A1* | 11/2008 | de Lorenzo Prieto | ........................ C07K 14/245 435/252.3 |
| 2009/0155275 A1* | 6/2009 | Wu | ........................ C07K 16/468 424/136.1 |
| 2009/0169548 A1 | 7/2009 | Grosveld et al. | |
| 2009/0208502 A1 | 8/2009 | Willemsen | |
| 2009/0268502 A1 | 10/2009 | Miura et al. | |
| 2009/0269277 A1 | 10/2009 | Chang et al. | |
| 2009/0304693 A1 | 12/2009 | Ghayur et al. | |
| 2010/0029497 A1 | 2/2010 | Himmler et al. | |
| 2010/0062001 A1 | 3/2010 | Reiter et al. | |
| 2010/0158927 A1 | 6/2010 | Reiter et al. | |
| 2010/0228007 A1 | 9/2010 | Hoogenboom et al. | |
| 2010/0322935 A1 | 12/2010 | Croasdale et al. | |
| 2011/0059076 A1 | 3/2011 | McDonagh et al. | |
| 2011/0091446 A1 | 4/2011 | De et al. | |
| 2011/0110851 A1 | 5/2011 | Chang et al. | |
| 2011/0318369 A1 | 12/2011 | Reiter et al. | |
| 2012/0190828 A1* | 7/2012 | Jakobsen | ................. A61P 37/00 530/387.3 |
| 2012/0244578 A1* | 9/2012 | Kannan | ................... C07K 16/00 435/69.6 |
| 2013/0011375 A1 | 1/2013 | Chen | |
| 2013/0183307 A1 | 7/2013 | Renes et al. | |
| 2013/0202527 A1 | 8/2013 | Tse et al. | |
| 2014/0120090 A1* | 5/2014 | Willemsen | ............. C07K 16/30 424/134.1 |
| 2014/0205599 A1 | 7/2014 | Willemsen et al. | |
| 2014/0227273 A1 | 8/2014 | Willemsen et al. | |
| 2014/0336475 A1 | 11/2014 | Renes | |
| 2015/0056198 A1 | 2/2015 | Renes et al. | |
| 2015/0175683 A1 | 6/2015 | Renes et al. | |
| 2015/0202318 A1 | 7/2015 | Renes et al. | |
| 2017/0114144 A1 | 4/2017 | Willemsen | |
| 2018/0071398 A1 | 3/2018 | Willemsen et al. | |
| 2018/0105587 A1 | 4/2018 | Renes et al. | |

FOREIGN PATENT DOCUMENTS

| | | | | |
|---|---|---|---|---|
| GB | 1380341 A | 1/1975 | | |
| JP | 2003-525016 A | 8/2003 | | |
| JP | 2005-501517 A | 1/2005 | | |
| JP | 2005-504524 A | 2/2005 | | |
| JP | 2005-521389 A | 7/2005 | | |
| JP | 2005-533486 A | 11/2005 | | |
| JP | 2006-523437 A | 10/2006 | | |
| JP | 2008-501781 A | 1/2008 | | |
| JP | 2008-523783 A | 7/2008 | | |
| JP | 2009-515897 A | 4/2009 | | |
| JP | 2009-524422 A | 7/2009 | | |
| JP | 2009-541361 | 11/2009 | | |
| JP | 2010-154864 A | 7/2010 | | |
| JP | 2010-535032 A | 11/2010 | | |
| JP | 2011-063603 A | 3/2011 | | |
| JP | 2011-097943 A | 5/2011 | | |
| JP | 2012-528092 A | 11/2012 | | |
| JP | 2014-505471 A | 3/2014 | | |
| WO | 92/01699 A1 | 2/1992 | | |
| WO | 96/35696 A1 | 11/1996 | | |
| WO | 98/45304 A1 | 10/1998 | | |
| WO | 99/08108 A1 | 2/1999 | | |
| WO | 99/42077 A2 | 8/1999 | | |
| WO | 00/23087 A1 | 4/2000 | | |
| WO | 00/31239 A1 | 6/2000 | | |
| WO | WO-0031239 A1 * | 6/2000 | ......... A61K 39/0011 | |
| WO | 02/79222 A2 | 10/2002 | | |
| WO | 02/83738 A1 | 10/2002 | | |
| WO | 03/40722 | 5/2003 | | |
| WO | 03/68201 A2 | 8/2003 | | |
| WO | 03/83124 A2 | 10/2003 | | |
| WO | 03/89467 A1 | 10/2003 | | |
| WO | 2004/003019 A2 | 1/2004 | | |
| WO | 2004/050705 A2 | 6/2004 | | |
| WO | WO-2004106380 A2 * | 12/2004 | ............ C07K 16/24 | |
| WO | 2005/113595 | 12/2005 | | |
| WO | 2005/120166 A2 | 12/2005 | | |
| WO | WO-2006037960 A2 * | 4/2006 | ......... C07K 14/7051 | |
| WO | 2007/059082 A1 | 5/2007 | | |
| WO | 2007073147 A1 | 6/2007 | | |
| WO | 2007/085837 A1 | 8/2007 | | |
| WO | 2008/120202 A2 | 10/2008 | | |
| WO | 2009/018386 A1 | 2/2009 | | |
| WO | 2009058383 A2 | 5/2009 | | |
| WO | 20091131435 A1 | 10/2009 | | |
| WO | 2009149185 A2 | 12/2009 | | |
| WO | WO-2010037838 A2 * | 4/2010 | ......... C07K 16/2803 | |
| WO | WO-2010133828 A1 * | 11/2010 | ......... C07K 14/7051 | |
| WO | 2010/136172 A1 | 12/2010 | | |
| WO | 20111001152 A1 | 1/2011 | | |
| WO | WO2011063348 * | 5/2011 | | |
| WO | 2011064664 A2 | 6/2011 | | |
| WO | 20111085473 A1 | 7/2011 | | |
| WO | 2012091564 A2 | 7/2012 | | |
| WO | 20121091563 A1 | 7/2012 | | |
| WO | 2013048243 A1 | 4/2013 | | |
| WO | 20131105856 A1 | 7/2013 | | |
| WO | 2014003552 A1 | 1/2014 | | |

OTHER PUBLICATIONS

Stork et al., Protein Engineering, Design & Selection vol. 20 No. 11 pp. 569-576, 2007.*
Wang et al., J. Biochem 135:555-565, 2004.*
Hudson et al., J Immunological Methods 231: 177-189, 1999.*
Davies et al., Protein Engineering 9(6): 531-537, 1996.*
Chames et al., PNAS 97(14): 7969-7974 (Year: 2000).*
Muyldermans et al., Reviews in Molecular Biotechnology 74: 277-302 (Year: 2001).*
Lloyd et al., Protein Engineering, Design & Selection 22: 159-168 (Year: 2009).*
Edwards et al., J Mol Biol 334(1): 103-118 (Year: 2003).*
Nguyen et al., EMBO J 19(5): 921-930 (Year: 2000).*
International Search Report for Patent Cooperation Treaty Application No. PCT/NL2012/050675, dated Jan. 2, 2013, 5 pages.
Saerens, D., et al., "Single-domain antibodies as building blocks for novel therapeutics," Current Opinion in Pharmacology, 2008, vol. 8 pp. 600-608.
Hudson, P. et al., High acidity scFv multimers; diabodies and triabodies, Journal of Immunological Methods, 1999, 231,177-189.
Japanese Notification for Reason of Refusal dated Jun. 24, 2016, 4 pages.
Jongmans, W. et al., Targeting of Adenovirus to human renal cell carcinoma cells, Urology, 2003, 62,559-565.
Jung, G. et al., and Target. cell induced T cell activation with bi- and trispecific antibody fragments, European Journal of Immunology, 1991**,21,2431.
Kurogiet al., An antibody therapy of cancer besides, Biotherapy, 2005, 19 (2), 125-132.
Liu, J. et. al., A new format of single chain tri-specific antibody with diminished molecular size sufficiently infuses ovarian tumor cell killing, Biotechnology Letters, 2005, 27, 1821-1827.
Saerens D. et al., Single-domain antibodies as building blocks for novel therapeutics, and Current Opinion. in Pharmacology, 2008, 8,600-608.
Schmidt M. et. al., Targeted inhibition of tumor cell growth by a bispecific single chain toxin containing an antibody domain and TGFalpha, British Journal of Cancer, 1996, 74,853-862.
Schoonjans R. et. al., Fab Chains As an Efficient Heterodimerization Scaffold for the Production of Recombinant Bispecific and TrispecificAntibody Derivatives, The Journal of Immunology, 2000, 165, 7050-7057.
Segal, DM. et al., and Introduction: bispecific antibodies, Journal of Immunological Methods, and 2001**,248,1-6.
Stork, R. et. al., A novel tri-functional antibody fusion protein with improved pharmacolonetic properties generated by fusing a bispecific single-chain diabody. with an albumin-binding domain from streptococcal protein G, Protein Engineering, Design & Selection,2007, 20 (11), 569-576.

(56) References Cited

OTHER PUBLICATIONS

Wang, X. et. al., A new Recombinant Single Chain Trispecific Antibody Recruits T lymphocytes to Kill CEA (Carcinoma Embryonic Antigen) Positive Tumor Cells In Vitro Efficiently, Journal of Biochemistry, 2004, 135 (4) 555-565.
Newton et al., Signaling in Innate Immunity and Inflammation, 2012, pp. 1-19, Cold Spring Harbor.
Pathogen-associate molecular pattern, Wikipedia, available at : https://en.wikipedia.org/wiki/Pathogen-associated_molecular_pattern, visited May 25, 2017.
PCT International Search Report, PCT/NL2013/050453, dated Oct. 21, 2013.
Willemsen et al., Cytometry, 2008, vol. 73A, pp. 1093-1099.
Ping et al., The Journal of Biological Chemistry, Jun. 1, 2012, vol. 287, pp. 19399-19408.
PCT Written Opinion PCT/NL2013/050453, dated Oct. 21, 2013.
PCT International Preliminary Report on Patentability, PCT/NL2013/050453, dated Dec. 31, 2014.
Brorson et al., J. Immunol., 1999, vol. 163, pp. 6694-6701.
Abaza et al. (Journal of Protein Chemistry, vol. 11, No. 5, 1992, pp. 433-444.
Zarour et al (Cancer Res., 2000, 60: 4946-4952).
Willemsen et al: "A phage display selected Fab fragment with MHC class I-restricted specificity for MAGE-A1 allows for retargeting of primary human T lymphocytes", Gene Therapy, vol. 8, No. 21, Nov. 1, 2001 (Nov. 1, 2001), pp. 1601-1608, XP55028813, ISSN: 0969-7128, DOI: 10.1038/sj.gt.3301570 the whole document.
Ward et al. (Nature 341:544-546 (1989)).
Vincke & Muyldermans, Chapter 2 in: Single Domain Antibodies: Methods and Protocols, D. Saerens & S. Muyldermans, eds, Methods Mol. Biol. 911:15-26 (2012).
Vajdos et al. ((2002) J. Mol. Biol. 320, 415-428).
Stish et al., Increasing Anticarcinoma Activity of an Anti-erbB2 Recombinant Immunotoxin by the Addition of an Anti-EpCAM sFv, Clinical Cancer Research, May 15, 2007, pp. 3058-3067, vol. 13, No. 10.
Song et al. (Biochem Biophys Res Comm 268:390-394 (2000)).
Smith-Gill et al. (J. Immunol. 139:4135-4144 (1987)).
Sekimoto et al. (Cancer Res 2007; 67: (3): 1184-1192; Feb. 1, 2007).
Paul, Fundamental Immunology, 3rd Edition, 1993, pp. 292-295.
Ozaki S. ((2011) Diabody. In: Schwab M. (eds) Encyclopedia of Cancer. Springer, Berlin, Heidelberg; definition of "diabody"; link. springer.com/referenceworkentry/10.1007%2F978-3-642-16483-5_1603).
Muraoka et al (J. Biochem. 2009; 145(6)799-810).
Monegal et al., Protein Design & Selection, 2009; 22(4):273-280.
Michaeli et al., Expression Hierarchy of T Cell Epitopes from Melanoma Differentiation Antigens: Unexpected High Level Presentation of Tyrosinase-HLA-A2 Compiexes Revealed by Peptide-Specific, MHC-Restricted, TCR-Like Antibodies, The Journal of Immunology, May 15, 2009, pp. 6328-6241, vol. 182, No. 10, The American Association of Immunologists, US.
Mareeva et al., Antibody Specific for the PeptideMajor Histocompatibility Complex: Is it T cell receptor-like? Journal of Biological Chemistry, Oct. 22, 2004, pp. 44243-44249, vol. 279, No. 43, American Society for Biochemistry and Molecular Biology, US.
MacCallum et al., J. Mole Biol. 1996, vol. 262, pp. 732-745.
Li et al. "Construction and characterization of a humanized anti-human CD3 monoclonal antibody 12F6 with effective immunoregulation functions" Article (2005) pp. 487-498, Immunology 116: 487-498, 2005.
Lev et al., Isolation and Characterization of Human Recombinant Antibodies Endowed with the Antigen-specific, Major Histocompatibility Complex-restricted Specificity of T Cells Directed toward the Widely Expressed Tumor T-cell Epitopes of the Telomerase Catalytic Subunit, Cancer Research, Jun. 1, 2002, pp. 3184-3194, vol. 62, American Association for Cancer Research.
Kumar et al. (J. Biol. Chem. 275:35129-35136 (2000)).
Kobayashi et al. (Protein Engineering 12:879-844 (1999)).
Kawakami, Yutaka, Identification of Human Melanoma Antigens Recognized by T Cells and Their Use For Immune-Gene Therapy, http://www.jstage.jst.go.jp/article/jslrt1997/37/3/37_3_137_article/-ch . . . Visited Sep. 28, 2018, J Immunother Emphasis tumor Immunol 14(2): 88-93, 1993.
Jang et al., Mclec. Immunol., 1998, vol. 35, pp. 1207-1217.
Jager et al. (PNAS, 2000, 97(22): 12198-12203).
International Search Report, PCT/NL2013/050014, dated Jun. 4, 2013.
International Search Report and Written Opinion received for PCT Patent Application No. PCT/NL2011/050893, dated Jun. 6, 2012, 9 pages.
International Search Report and Written Opinion received for PCT Patent Application No. PCT/NL11/50891, dated Jun. 12, 2012, 11 pages.
International Preliminary Report on Patentability received for PCT Patent Application No. PCT/NL2012/050675, dated Apr. 10, 2014, 6 pages.
International Preliminary Report on Patentability received for PCT Patent Application No. PCT/NL2011/050893, dated Jul. 11, 2013, 7 pages.
International Preliminary Report on Patentability received for PCT Patent Application No. PCT/NL11/50891, dated Jul. 11, 2013, 8 pages.
Ibragimova and Wade (Biophysical Journal,, 1999, 77, 2191-2198.
Holm et al., 2007, Mol. Immunol., vol. 44, pp. 1075-1084.
Hickman, Cancer and Metastasis Reviews 11:121 1992.
Harmsen et al., Properties, production, and applications of camelid single-domain antibody fragments, Appl Microbial Biotechnol, (2007), 77: pp. 13-22.
Gussow et al. (1991, Methods in Enzymology 203:99-121).
Graff-Dubois et al. (Graff J. Immunol, 2002, 169, 575-80).
Gatz et al. ("Gatz", Tissue Antigens, 2002, 55, 532-547).
Dunbar et al. Examining Variable Domain Orientations in Antigen Receptors Gives Insight into TCR-Like Antibody Design LOA computational Biology, www.ploscompbiol.org, Article dated Sep. 2014; vol. 10 Issue 9, (10 pages).
Ducry et al. ("Ducry", Bioconjugate Chem. 2010, 21, 5-13).
Dorvillius et al., Targeting of Human Breast Cancer by a Bispecific Antibody Directed Against Two Tumour-Associated Antigens: ERBB-2 and carcinoembryonic Antigen, Tumor Biology, Jan. 1, 2002, pp. 337-347, vol. 23, Karger, Basel, CH.
Denkberg et al., Selective Targeting of Melanoma and APCs Using a Recombinant Antibody with TCR-Like Specificity Directed Toward a Melanoma Differentiation Antigen, The Journal of Immunology, 2003, 171: pp. 2197-2207.
De Pascalis et al., Grafting of "Abbreviated" Complementarity-Determining Regions Containing Specificity-Determining Residues Essential for Ligand Contact to Engineer a Less Immunogenic Humanized Monoclonal Antibody, The Journal of Immunology, 2002, pp. 3076-3084, vol. 169.
Coleman et al. (Research in Immunology, 1994; 145(1): 33-36).
Cohen et al., Direct detection and quantitation of a distinct T-cell epitope derived from tumor-specific epithelial cell-associated mucin using human recombinant antibodies endowed with the antigen-specific, . . . complex-restricted specificity of T-cells, Cancer Research, Oct. 15, 2002, pp. 5835-5844, vol. 62, American Association for Cancer Research, US.
Chomez et al., An Overview of the MAGE Gene Family with the Identification of All Human Members of the Family, Jul. 15, 2001, Cancer Research 61, pp. 5544-5551.
Chinnasamy et al., J. Immunol. 2011; 186:685-96 (pub'd online Dec. 13, 2010).
Chen et al. J. Mol. Bio. (1999) 293, 865-881.
Chames et al., TCR-like human antibodies expressed on human CTLs mediate antibody affinity-dependent cytolytic activity, The Journal of Immunology, Jul. 15, 2002, pp. 1110-1118, vol. 169, No. 2, The American Association of Immunologists, US.
Casset et al., A peptide mimetic of an anti-CD4 monoclonal antibody by rational design, BBRC, 2003, pp. 198-205, vol. 307, Elsevier.
Burks et al. (PNAS 94:412-417 (1997)).
Brummell et al. (Biochemistry 32:1180-1187 (1993)).

(56) References Cited

OTHER PUBLICATIONS

Chinnasamy N et al and A TCR targeting the HLA-A*0201-restricted epitope of MAGE-A3 recognizes multiple epitopes of the MAGE-A antigen superfamily in several types of cancer, J Immunology, 2011, vol. 186,685-696.
Ducry L & Stump B, Antibody-drug conjugates: linking cytotoxic payloads to monoclonal antibodies and Bioconjug Chem, 2010, and vol. 21 No. 1, 5-13.
European Extended Search Report and Opinion for European Application No. 18202044.6, dated Feb. 14, 2019, 10 pages.
European Search Report and Search Opinion Received for EP Application No. 18207894, dated Feb. 4, 2019, 10 pages.
Graff-Dubois S et al: "Generation of CTL Recognizing an HLA-A 0201-Restricted Epitope Shared by MAGE-A1, -A2, -A3, -A4,-A6, -A10, and -A12 Tumor Antigens: Implication in a Broad-Spectrum Tumor Immunotherapy", The Journal of Immunology, The American Association of Immunologists, US, vol. 169, No. 1, Jan. 1, 2002 (Jan. 1, 2002), pp. 575-580.
Holliger et al., "Engineered antibody fragments and the rise of single domains", Nat Biotechnol., vol. 23, No. 9, (Sep. 2005), pp. 1126-1136.
Houghton et al., N.E., Immunity against cancer: lessons learned from melanoma. Curr Opin Immunol 2001, 13, 134-40.
Isolation and identification of human melanoma antigens recognized by Kawakami, T cells, application for immunogene therapy, Journal of the Japan Lymphoreticular System, 1997, vol. 37, No. 3, pp. 137-144.
Japanese Decision of Refusal for Japanese Application No. 2014-533232, dated May 9, 2017, 6 pages with English Translation.
Japanese Notice of Reasons for Refusal for Japanese Application No. 2014-533232, dated Jun. 24, 2016, 8 pages with English Translation.
Japanese Notice of Reasons for Refusal for Japanese Application No. 2017-173519, dated Oct. 2, 2018, 10 pages with English Translation.
Japanese Search Report for Japanese Application No. 2014-533232, dated Jun. 23, 2016, 37 pages With English Translation.
Klechevsky E et al and Antitumor activity of immunotoxinswith Tcell receptor-like apecificity against human melanoma xenografts, Cancer Res, 2008, vol. 68 No. 15-6360-6367.
Masaaki Satoh et al: "Monoclonal Antibody 2-152a Suppresses Hepatitis C Virus Infection Through Betaine/Gaba Transporter-1", Journal of Nfectious Diseases. JID, vol. 204, No. 8, Oct. 15, 2011 (Oct. 15, 2011), pp. 1172-1180.
Parmiani et al. "Unique human tumor antigens: immunobiology and use in clinical trials", J Immunol 2007, 178, 1975-9.
Reynolds Gary Met Al: "Hepatitis C virus receptor expression in normal and diseased liver tissue", Hepatology, John Wiley & Sons, Inc, US, vol. 47, No. 2, Feb. 1, 2008 (Feb. 1, 2008), pp. 418-427, XP002516760, ISSN: 0270-9139, DOI: 10.1002/HEP.22028.
Ridgway et al. "Knobs-into-holes" engineering of antibody CH3 domains for heavy chain heterodimerization, Protein Engineering 1996, 9(7), 617-621.
The Journal of Immunology, 2011, and vol. 186 and pp. 685-696.
Van Den Eynde et al. "T cell-defined tumor antigens" Curr Opin Immunol 1997, 9, 684-93.
Arakawa et al., "Cloning and Sequencing of the VH and V Kappa Genes of an anti-CD3 Monoclonal Antibody, and Construction of a Mouse/Human Chimeric Antibody", j. Biochem, vol. 120, No. 3, (1996), pp. 657-662.
Cao et al., "Targeting Cell Surface (Beta2)-Microglobulin by Pentameric IgM Antibodies," Br. J. Haematol., vol. 154, (2011), pp. 111-121.
Chames et al. "Selection of Antibodies Against Biotinylated Antigens" Methods in Molecular Biology 2002, 178:147-159.
Chomczynski et al. "Single-Step Method of RNA Isolation by Acid Guanidinium Thiocyanate-Phenol-Chloroform Extraction" Anal. Biochem 1987. 162: 156-159.
Japanese Decision of Refusal for Japanese Application No. 2017-173519, dated Jul. 23, 2019, 9 pages with English Translation.

Japanese Written Opinion for Japanese Application No. 2017-173519, dated Apr. 9, 2019, 8 pages with English Translation.
Mattes et al., "Induction of Apoptosis by Cross-Linking Antibodies Bound to Human B-Lymphoma Cells: Expression of Annexin V Binding Sites on the Antibody Cap," Cancer Biotherapy and Radiopharmaceuticals, vol. 24, (2009), pp. 185-193.
Pedersen et al, "MHC-I-Induced Apoptosis in Human B-Lymphoma Cells is Dependent on Protein Tyrosine and Serine/Threonine Kinases," Experimental Cell Research, vol. 251, (1999), pp. 128-134.
Riechmann et al. "Single domain antibodies: comparison of camel VH and camelised human VH domains" Journal of Immunological Methods 1999, 231:25-38.
Traversari et al. "A Nonapeptide Encoded by Human Gene MAGE-1 Is Recognized on HLA-A1 by Cytolytic T Lymphocytes Directed against Tumor Antigen MZ2-E" J. Exp. Med 1992, 176:1453-1457.
Wallen-Ohman et al., "A Cell Surface Antigen (BAL) Defined by a Mouse Monoclonal Antibody Inducing Apoptosis in a Human Lymphocytic Leukemia Cell Line," Int. J. Cancer, vol. 57, (1994), pp. 544-552.
Yang et al., "Killing Tumor Cells Via Their Surface (Beta2)M or MHC class I Molecules," Cancer, vol. 116, (2010), pp. 1638-1645.
Bent Jakobsen: "Immunocore powerpoint presentation", iSBTc Washington, Oct. 30, 2009 (Oct. 30, 2009), pp. 1-19, XP055485474, Retrieved from the Internet: URL:https://sitc.sitcancer.org/meetings/am09/presentations/fri/Jakobsen.pdf [retrieved on Jun. 19, 2018].
Claude Backendorf et al: "Apoptin: Therapeutic Potential of an Early Sensor of Carcinogenic Transformation", Annual Review of Pharmacology and Toxicology, vol. 48, No. 1, Feb. 1, 2008 (Feb. 1, 2008), pp. 143-169, XP055139454, ISSN: 0362-1642, DOI: 10.1146/annurev.pharmtox.48.121806.154910.
European Communication pursuant to Article 94(3) EPC for European Application No. 11820898, dated Jun. 20, 2016, 7 pages.
European Communication pursuant to Article 94(3) EPC for European Application No. 11820898, dated Sep. 11, 2018, 5 pages.
European Communication pursuant to Article 94(3) EPC for European Application No. 11820898, dated Sep. 16, 2014, 6 pages.
European Communication pursuant to Article 94(3) EPC for European Application No. 11820898, dated Sep. 21, 2017, 6 pages.
European Communication pursuant to Article 94(3) EPC for European Application No. 11820899, dated Aug. 4, 2016, 4 pages.
European Communication pursuant to Article 94(3) EPC for European Application No. 11820899, dated Mar. 20, 2018, 3 pages.
European Communication pursuant to Article 94(3) EPC for European Application No. 11820899, dated Nov. 17, 2015, 3 pages.
European Communication pursuant to Article 94(3) EPC for European Application No. 12772530, dated Jan. 27, 2016, 3 pages.
European Communication pursuant to Article 94(3) EPC for European Application No. 13703480, dated Aug. 24, 2015, 4 pages.
European Communication pursuant to Article 94(3) EPC for European Application No. 13703480, dated Oct. 7, 2016, 5 pages.
European Communication pursuant to Article 94(3) EPC for European Application No. 13703480, dated Sep. 20, 2017, 5 pages.
European Communication pursuant to Article 94(3) EPC for European Application No. 13737682, dated Feb. 17, 2017, 5 pages.
European Communication pursuant to Article 94(3) EPC for European Application No. 13737682, dated May 2, 2016, 5 pages.
European Search and Opinion for European Application No. 18153459, dated Jun. 28, 2018, 9 pages.
H-Y Zhang et al: "Tumor-targeted delivery of biologically active TRAIL protein", Cancer Gene Therapy, Appleton & Lange, GB, vol. 17, May 1, 2010 (May 1, 2010), pp. 334-343, XP002660326, ISSN: 0929-1903, DOI: 10.1038/CGT2009.76 [retrieved on Jan. 15, 2010].
K. Breckpot et al: "Identification of New Antigenic Peptide Presented by HLA-Cw7 and Encoded by Several MAGE Genes Using Dendritic Cells Transduced with Lentiviruses", The Journal of Immunology, vol. 172, No. 4, Feb. 5, 2004 (Feb. 5, 2004), pp. 2232-2237, XP055485920, us ISSN: 0022-1767, DOI: 10.4049/jimmunol.172.4.2232.
Nathaniel Liddy et al: "Monoclonal TCR-redirected tumor cell killing", Nature Medicine, vol. 18, No. 6, May 6, 2012 (May 6, 2012), pp. 980-987, XP055241791 New York ISSN: 1078-8956, DOI: 10.1038/nm.2764.

(56) References Cited

OTHER PUBLICATIONS

Noy R et al: "T-Cell Receptor-Like Antibodies: Novel Reagents for Clinical Cancer Immunology and Immunotherapy", Expert Review of Anticancer the, Expert Reviews LTD, GB, vol. 5, No. 3, Jun. 1, 2005 (Jun. 1, 2005), pp. 523-536, XP009067037, ISSN: 1473-7140, DOI: 10.1586/14737140.5.3523.
P Bruno et al: "Family at last: highlights of the first international meeting on proteins killing tumour cells", Cell Death and Differentiation., vol. 16, No. 1, Jan. 1, 2009 (Jan. 1, 2009), pp. 184-186, XP55407217, GB ISSN: 1350-9047, DOI: 10.1038/cdd.2008.164.
Reynolds Gary M et al: "Hepatitis C virus receptor expression in normal and diseased liver tissue", Hepatology, Wiley, vol. 47, No. 2, Feb. 1, 2008 (Feb. 1, 2008 ), pp. 418-427, XP002516760.
Stieglmaier Julia et al: "Selective induction of apoptosis in leukemic B-lymphoid cells by a CD19-specific TRAIL fusion protein", Cancer Immunology, Immunotherapy, Springer, Berlin/Heidelberg, vol. 57, No. 2, Feb. 1, 2008 (Feb. 1, 2008), pp. 233-246, XP002528355, ISSN: 0340-7004, DOI: 10.1007/S00262-007-0370-8 [retrieved on Jul. 31, 2007].
Engler et al; (Vaccine, 2004, p. 58-68).
Danen-Van Oorschot et al. "Apoptin induces apoptosis in human transformed and malignant cells but not in normal cells" Proc. Nat'l Acad. Sci., USA vol. 94, pp. 5843-5847 (1997).
De Haard et al. "A Large Non immunized Human Fab Fragment Phage Library That Permits Rapid Isolation and Kinetic Analysis of High Affinity Antibodies" The Journal of Biological Chemistry, 1999, 274:18218-18230.
Li et al. "Antitumor effects of a recombinant fowlpox virus expressing Apoptin in vivo and in vitro" Int. J. Cancer 119(12):2948-57 (2006).

Marcar et al. "Mage-A cancer/testis antigens inhibit p53 function by blocking its interaction with chromatin" Cancer Res. 2010, 70:10362-10370.
McCurdy et al. "Expression of melanoma antigen gene by cells from inflamed joints in juvenile rheumatoid arthritis" J. Rheumatol. 2002, 29:2219-2224 (Abstract Only).
Noteborn, "Proteins selectively killing tumor cells" Eur. J. Pharmacol., 2009, 625:165 173 (Abstract Only).
Olijslagers et al. "Additive cytotoxic effect of apoptin and chemotherapeutic agents paclitaxel and etoposide on human tumour cells" .Basic Clin. Pharmacol. Toxicol. 100(2):127-31.
Park et al, "Expression of MAGE-A and NY-ES0-1 in Primary and Metastatic Cancers" J Immunother. Jan. 2016; 39(1): 1-7.
Vyas et al. "The Known Unknowns of Antigen Processing and Presentation" Nature Reviews Immunology, vol. 8, Aug. 2008, 607-618.
Communication pursuant to Article 94(3) EPC for European Application No. 18153459, dated Feb. 18, 2020, 5 pages.
European Communication pursuant to Article 94(3) EPC for European Application No. 18202044, dated Feb. 18, 2020, 7 pages.
Renkvist et al. "A listing of human tumor antigens recognized by T cells" Cancer Immunol. Immunother. 2001; 50: 3 15.
Teicher et al, Antibody conjugate therapeutics: challenges and potential. Clin. Cancer Res., 2011, 17(20):6389 97.
Yang et al. "Chimeric immune receptors (CIRs) specific to JC virus for immunotherapy in progressive multifocal leukoencephalopathy (PML)" International Immunology, vol. 19, No. 9, pp. 1083-1093).
Henry et al (Frontiers in Immunology 8:1-15 (Dec. 12, 2017).
Kim et al. (Biochimica et Biophysica Acta 1844 (2014) 1983-2001).

\* cited by examiner

Fig. 1

6. {$(D1)_{1-6}$, $(D2)_{1-6}$, $(D3)_{1-6}$, effector moiety}, for example $(D1)_{1-6}$ - $(D2)_{1-6}$ - $(D3)_{1-6}$ - effector moiety, for example $(D1)_2$ - $(D2)_2$ - $(D3)_2$ - effector moiety {$(D1)_{1-6}$, $(D2)_{1-6}$, $(D3)_{1-6}$, $(D4)_{1-6}$, effector moiety}, for example $(D1)_{1-6}$ - $(D2)_{1-6}$ - $(D3)_{1-6}$ - $(D4)_{1-6}$ - effector moiety, for example $(D1)$ - $(D2)_2$ - $(D3)_2$ - $(D4)$ - effector moiety {$(D1)_{1-6}$, $(D2)_{1-6}$, $(D3)_{1-6}$, $(D4)_{1-6}$, $(D5)_{1-6}$, effector moiety}, for example $(D1)_{1-6}$ - $(D2)_{1-6}$ - $(D3)_{1-6}$ - $(D4)_{1-6}$ - $(D5)_{1-6}$ - effector moiety, for example $(D1)_2$ - $(D2)$ - $(D3)$ - $(D4)$ - $(D5)_2$ - effector moiety {$(D1)_{1-6}$, $(D2)_{1-6}$, $(D3)_{1-6}$, $(D4)_{1-6}$, $(D5)_{1-6}$, $(D6)_{1-6}$, effector moiety}, for example $(D1)_{1-6}$ - $(D2)_{1-6}$ - $(D3)_{1-6}$ - $(D4)_{1-6}$ - $(D5)_{1-6}$ - $(D6)_{1-6}$ - effector moiety, for example $(D1)_2$ - $(D2)$ - $(D3)_2$ - $(D4)$ - $(D5)_2$ - $(D6)$ - effector moiety

2. {D1, (D2)$_{3-6}$}, for example D1 - (D2)$_{3-6}$, or (D2)$_{3-6}$ - D1

3. {(D1)$_{2-6}$, (D2)$_{2-6}$}, for example (D1)$_{2-6}$ - (D2)$_{2-6}$, for example (D1)$_2$ - (D2)$_2$

4. {(D1)$_{1-6}$, (D2)$_{1-6}$, (D3)$_{1-6}$}, for example (D1)$_{1-6}$ - (D2)$_{1-6}$ - (D3)$_{1-6}$, for example (D1)$_2$ - (D2)$_2$ - (D3)$_2$

{(D1)$_{1-6}$, (D2)$_{1-6}$, (D3)$_{1-6}$, (D4)$_{1-6}$}, for example (D1)$_{1-6}$ - (D2)$_{1-6}$ - (D3)$_{1-6}$ - (D4)$_{1-6}$, for example (D1)$_2$ - (D2) - (D3) - (D4)$_2$

{(D1)$_{1-6}$, (D2)$_{1-6}$, (D3)$_{1-6}$, (D4)$_{1-6}$, (D5)$_{1-6}$}, for example (D1)$_{1-6}$ - (D2)$_{1-6}$ - (D3)$_{1-6}$ - (D4)$_{1-6}$ - (D5)$_{1-6}$, for example (D1)$_2$ - (D2) - (D3)$_2$ - (D4) - (D5)$_2$ {(D1)$_{1-6}$, (D2)$_{1-6}$, (D3)$_{1-6}$, (D4)$_{1-6}$, (D5)$_{1-6}$, (D6)$_{1-6}$}, for example (D1)$_{1-6}$ - (D2)$_{1-6}$ - (D3)$_{1-6}$ - (D4)$_{1-6}$ - (D5)$_{1-6}$ - (D6)$_{1-6}$, for example (D1) - (D2) - (D3) - (D4) - (D5) - (D6)

5. {(D1)1-6, (D2)1-6, effector moiety}, for example (D1)$_{1-6}$ - (D2)$_{1-6}$ - effector moiety, for example (D1)$_2$ - (D2)$_2$ - effector moiety

SEQUENCE LISTING

```
<160> NUMBER OF SEQ ID NOS: 51

<210> SEQ ID NO 1
<211> LENGTH: 417
<212> TYPE: DNA
<213> ORGANISM: Artificial
<220> FEATURE:
<223> OTHER INFORMATION: Synthetic

<400> SEQUENCE: 1
atgaacatgc tgactgccag cctgttgagg gcagtcatag cctccatctg tgttgtatcc      60
agcatggctc agaaggtaac tcaagcgcag actgaaattt ctgtggtgga gaaggaggat     120
gtgaccttgg actgtgtgta tgaaaccgt gatactactt attacttatt ctggtacaag      180
caaccaccaa gtggagaatt ggttttcctt attcgtcgga actcttttga tgagcaaaat     240
gaaataagtg gtcggtattc ttggaacttc cagaaatcca ccagttcctt caacttcacc     300
atcacagcct cacaagtcgt ggactcagca gtatacttct gtgctctggg aggggtgaat     360
aataatgcag gcaacatgct cacctttgga gggggaacaa ggttaatggt caaaccc       417

<210> SEQ ID NO 2
<211> LENGTH: 396
<212> TYPE: DNA
<213> ORGANISM: Artificial
<220> FEATURE:
<223> OTHER INFORMATION: Synthetic

<400> SEQUENCE: 2
atgggcttca ggctgctctg ctgtgtggcc ttttgtctcc tgggagcagg cccagtggat      60
tctggagtca cacaaacccc aaagcacctg atcacagcaa ctgacagcg agtgacgctg     120 agatgctccc ctaggtctgg agacctctct gtgtactggt accaacagag cctggaccag     180
ggcctccagt tcctcattca ctattataat ggagaagaga gagcaaaagg aaacattctt     240
gaacgattct ccgcacaaca gttccctgac ttgcactctg aactaaacct gagctctctg     300
gagctggggg actcagcttt gtatttctgt gccagcaaca tagcgggcgg gagttatacg     360
cagtattttg gcccaggcac ccggctgaca gtgctc                              396

<210> SEQ ID NO 3
<211> LENGTH: 897
<212> TYPE: DNA
<213> ORGANISM: Artificial
<220> FEATURE:
<223> OTHER INFORMATION: Synthetic
```

<400> SEQUENCE: 3

```
atgaaatacc tattgcctac ggcagccgct ggattgttat tactcgcggc ccagccggcc    60
atggcccagc tgcagctgca ggagtccggg ggaggcgtgg tccagcctgg gaggtccctg   120
agactctcct gtgcagcctc tggattcacc ttcagtagct atggcatgca ctgggtccgc   180
caggctccag gcaaggagag agaggggtg gcagttatat catatgatgg agtaataaa    240
tactatgcag actccgtgaa gggccgattc accatctcca gagacaattc caagaacacg   300
ctgtatctgc aaatgaacag cctgagagct gaggacacgg ctgtgtatta ctgtgccggt   360
gggagctact acgtcccgga ctactgggc cagggaaccc tggtcaccgt ctcaagcgcg    420
gccgcaggtg gcggagggtc tggtggcgga gggtctggtg cggagggtc gcaggtgcag    480
ctgcagcagt ctggggctga actggcaaga cctggggcct cagtgaagat gtcctgcaag   540
gcttctggct acacctttac taggtacacg atgcactggg taaaacagag gcctggacag   600
ggtctggaat ggattggata cattaatcct agccgtggtt atactaatta caatcagaag   660
ttcaaggaca aggccacatt gactacagac aaatcctcca gcacagccta catgcaactg   720
agcagcctga catctgagga ctctgcagtc tattactgtg caagatatta tgatgatcat   780
tactgccttg actactgggg ccaaggcacc actctcacag tctcctcagg ggccgcagaa   840
caaaaactca tctcagaaga ggatctgaat ggggcccatc atcatcatca tcactaa     897
```

<210> SEQ ID NO 4
<211> LENGTH: 298
<212> TYPE: PRT
<213> ORGANISM: Artificial
<220> FEATURE:
<223> OTHER INFORMATION: Synthetic

<400> SEQUENCE: 4

```
Met Lys Tyr Leu Leu Pro Thr Ala Ala Gly Leu Leu Leu Leu Ala
1               5                   10                  15

Ala Gln Pro Ala Met Ala Gln Leu Gln Leu Gln Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Glu Arg Glu Gly Val Ala Val Ile Ser Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Gly Gly Ser Tyr Tyr Val Pro Asp Tyr
        115                 120                 125

Trp Gly Gln Gly Thr Leu Val Thr Val Ser Ser Ala Ala Gly Gly
    130                 135                 140

Gly Gly Ser Gly Gly Gly Gly Ser Gly Gly Gly Gly Ser Gln Val Gln
145                 150                 155                 160

Leu Gln Gln Ser Gly Ala Glu Leu Ala Arg Pro Gly Ala Ser Val Lys
                165                 170                 175

Met Ser Cys Lys Ala Ser Gly Tyr Thr Phe Thr Arg Tyr Thr Met His
            180                 185                 190
```

Trp Val Lys Gln Arg Pro Gly Gln Gly Leu Glu Trp Ile Gly Tyr Ile
            195                 200                 205

Asn Pro Ser Arg Gly Tyr Thr Asn Tyr Asn Gln Lys Phe Lys Asp Lys
    210                 215                 220

Ala Thr Leu Thr Thr Asp Lys Ser Ser Thr Ala Tyr Met Gln Leu
225             230                 235                 240

Ser Ser Leu Thr Ser Glu Asp Ser Ala Val Tyr Tyr Cys Ala Arg Tyr
                245                 250                 255

Tyr Asp Asp His Tyr Cys Leu Asp Tyr Trp Gly Gln Gly Thr Thr Leu
            260                 265                 270

Thr Val Ser Ser Gly Ala Ala Glu Gln Lys Leu Ile Ser Glu Glu Asp
        275                 280                 285

Leu Asn Gly Ala His His His His His His
    290                 295

<210> SEQ ID NO 5
<211> LENGTH: 37
<212> TYPE: DNA
<213> ORGANISM: Artificial
<220> FEATURE:
<223> OTHER INFORMATION: PCR primer

<400> SEQUENCE: 5
gcgaattcta cgtaccatga acatgctgac tgccagc                         37

<210> SEQ ID NO 6
<211> LENGTH: 32
<212> TYPE: DNA
<213> ORGANISM: Artificial
<220> FEATURE:
<223> OTHER INFORMATION: PCR primer

<400> SEQUENCE: 6
cgtctagagg acagaaggta actcaagcgc ag                              32

<210> SEQ ID NO 7
<211> LENGTH: 36
<212> TYPE: DNA
<213> ORGANISM: Artificial
<220> FEATURE:
<223> OTHER INFORMATION: PCR primer

<400> SEQUENCE: 7
ccgaattcta cgtaccatgg gcttcaggct gctctg                          36

<210> SEQ ID NO 8
<211> LENGTH: 29
<212> TYPE: DNA
<213> ORGANISM: Artificial
<220> FEATURE:
<223> OTHER INFORMATION: PCR primer

<400> SEQUENCE: 8
gcggatccga gcactgtcag ccgggtgcc                                  29

<210> SEQ ID NO 9
<211> LENGTH: 84
<212> TYPE: DNA
<213> ORGANISM: Artificial
<220> FEATURE:
<223> OTHER INFORMATION: Linker 212

<400> SEQUENCE: 9

```
gtacgaattc gcagatctgg ctctacttcc ggtagcaaat cctctgaagg caaaggtact    60
agtgcggatc cggctcgagc agct                                           84
```

<210> SEQ ID NO 10
<211> LENGTH: 51
<212> TYPE: DNA
<213> ORGANISM: Artificial
<220> FEATURE:
<223> OTHER INFORMATION: Linker (GLY)4SER3

<400> SEQUENCE: 10

```
gatccggtgg aggcggttca ggcggaggtg gctctggcgg tggcggatcg a             51
```

<210> SEQ ID NO 11
<211> LENGTH: 5
<212> TYPE: PRT
<213> ORGANISM: Artificial
<220> FEATURE:
<223> OTHER INFORMATION: Linker polymer (GLY4SER)n

<400> SEQUENCE: 11

Gly Gly Gly Gly Ser
1               5

<210> SEQ ID NO 12
<211> LENGTH: 6
<212> TYPE: PRT
<213> ORGANISM: Artificial
<220> FEATURE:
<223> OTHER INFORMATION: Linker polymer (GlySerThrSerGlySer)n

<400> SEQUENCE: 12

Gly Ser Thr Ser Gly Ser
1               5

<210> SEQ ID NO 13
<211> LENGTH: 9
<212> TYPE: PRT
<213> ORGANISM: Artificial
<220> FEATURE:
<223> OTHER INFORMATION: Epitope

<400> SEQUENCE: 13

Phe Leu Phe Leu Leu Phe Phe Trp Leu
1               5

<210> SEQ ID NO 14
<211> LENGTH: 9
<212> TYPE: PRT
<213> ORGANISM: Artificial
<220> FEATURE:
<223> OTHER INFORMATION: Epitope

<400> SEQUENCE: 14

Thr Leu Met Ser Ala Met Thr Asn Leu
1               5

<210> SEQ ID NO 15
<211> LENGTH: 9
<212> TYPE: PRT
<213> ORGANISM: Artificial
<220> FEATURE:
<223> OTHER INFORMATION: Epitope

<400> SEQUENCE: 15

Ala Leu Asp Val Tyr Asn Gly Leu Leu

```
1               5

<210> SEQ ID NO 16
<211> LENGTH: 9
<212> TYPE: PRT
<213> ORGANISM: Artificial
<220> FEATURE:
<223> OTHER INFORMATION: Epitope

<400> SEQUENCE: 16

Ile Leu Leu Trp Gln Pro Ile Pro Val
1               5

<210> SEQ ID NO 17
<211> LENGTH: 9
<212> TYPE: PRT
<213> ORGANISM: Artificial
<220> FEATURE:
<223> OTHER INFORMATION: Epitope

<400> SEQUENCE: 17

Leu Leu Leu Gly Thr Ile His Ala Leu
1               5

<210> SEQ ID NO 18
<211> LENGTH: 33
<212> TYPE: PRT
<213> ORGANISM: Artificial
<220> FEATURE:
<223> OTHER INFORMATION: Epitope

<400> SEQUENCE: 18

Cys His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala

<210> SEQ ID NO 19
<211> LENGTH: 9
<212> TYPE: PRT
<213> ORGANISM: Artificial
<220> FEATURE:
<223> OTHER INFORMATION: Epitope

<400> SEQUENCE: 19

Lys Leu Gln Cys Val Asp Leu His Val
1               5

<210> SEQ ID NO 20
<211> LENGTH: 10
<212> TYPE: PRT
<213> ORGANISM: Artificial
<220> FEATURE:
<223> OTHER INFORMATION: Epitope

<400> SEQUENCE: 20

Phe Leu Thr Pro Lys Lys Leu Gln Cys Val
1               5                   10

<210> SEQ ID NO 21
<211> LENGTH: 10
<212> TYPE: PRT
<213> ORGANISM: Artificial
<220> FEATURE:
<223> OTHER INFORMATION: Epitope
```

```
<400> SEQUENCE: 21

Val Ile Ser Asn Asp Val Cys Ala Gln Val
1               5                   10

<210> SEQ ID NO 22
<211> LENGTH: 10
<212> TYPE: PRT
<213> ORGANISM: Artificial
<220> FEATURE:
<223> OTHER INFORMATION: Epitope

<400> SEQUENCE: 22

Tyr Ile Ser Asn Asp Val Cys Ala Gln Val
1               5                   10

<210> SEQ ID NO 23
<211> LENGTH: 9
<212> TYPE: PRT
<213> ORGANISM: Artificial
<220> FEATURE:
<223> OTHER INFORMATION: Epitope

<400> SEQUENCE: 23

Gln Val His Pro Gln Lys Val Thr Lys
1               5

<210> SEQ ID NO 24
<211> LENGTH: 9
<212> TYPE: PRT
<213> ORGANISM: Artificial
<220> FEATURE:
<223> OTHER INFORMATION: Epitope

<400> SEQUENCE: 24

Cys Tyr Ala Ser Gly Trp Gly Ser Ile
1               5

<210> SEQ ID NO 25
<211> LENGTH: 10
<212> TYPE: PRT
<213> ORGANISM: Artificial
<220> FEATURE:
<223> OTHER INFORMATION: Epitope

<400> SEQUENCE: 25

His Tyr Arg Lys Trp Ile Lys Asp Thr Ile
1               5                   10

<210> SEQ ID NO 26
<211> LENGTH: 9
<212> TYPE: PRT
<213> ORGANISM: Artificial
<220> FEATURE:
<223> OTHER INFORMATION: Epitope

<400> SEQUENCE: 26

Leu Leu His Glu Thr Asp Ser Ala Val
1               5

<210> SEQ ID NO 27
<211> LENGTH: 9
<212> TYPE: PRT
<213> ORGANISM: Artificial
<220> FEATURE:
<223> OTHER INFORMATION: Epitope
```

```
<400> SEQUENCE: 27

Ala Leu Phe Asp Ile Glu Ser Lys Val
1               5

<210> SEQ ID NO 28
<211> LENGTH: 9
<212> TYPE: PRT
<213> ORGANISM: Artificial
<220> FEATURE:
<223> OTHER INFORMATION: Epitope

<400> SEQUENCE: 28

Val Leu Ala Gly Gly Phe Phe Leu Leu
1               5

<210> SEQ ID NO 29
<211> LENGTH: 9
<212> TYPE: PRT
<213> ORGANISM: Artificial
<220> FEATURE:
<223> OTHER INFORMATION: Epitope

<400> SEQUENCE: 29

Asn Tyr Ala Arg Thr Glu Asp Phe Phe
1               5

<210> SEQ ID NO 30
<211> LENGTH: 9
<212> TYPE: PRT
<213> ORGANISM: Artificial
<220> FEATURE:
<223> OTHER INFORMATION: Epitope

<400> SEQUENCE: 30

Leu Tyr Ser Asp Pro Ala Asp Tyr Phe
1               5

<210> SEQ ID NO 31
<211> LENGTH: 9
<212> TYPE: PRT
<213> ORGANISM: Artificial
<220> FEATURE:
<223> OTHER INFORMATION: Epitope

<400> SEQUENCE: 31

Thr Tyr Ser Val Ser Phe Asp Ser Leu
1               5

<210> SEQ ID NO 32
<211> LENGTH: 9
<212> TYPE: PRT
<213> ORGANISM: Artificial
<220> FEATURE:
<223> OTHER INFORMATION: Epitope

<400> SEQUENCE: 32

Ala Leu Asp Val Tyr Asn Gly Leu Leu
1               5

<210> SEQ ID NO 33
<211> LENGTH: 9
<212> TYPE: PRT
<213> ORGANISM: Artificial
<220> FEATURE:
<223> OTHER INFORMATION: Epitope

<400> SEQUENCE: 33
```

```
Leu Tyr Cys Glu Ser Val His Asn Phe
1               5
```

<210> SEQ ID NO 34
<211> LENGTH: 15
<212> TYPE: PRT
<213> ORGANISM: Artificial
<220> FEATURE:
<223> OTHER INFORMATION: Epitope

<400> SEQUENCE: 34

```
Gly Gln Asp Leu Phe Gly Ile Trp Ser Lys Val Tyr Asp Pro Leu
1               5                   10                  15
```

<210> SEQ ID NO 35
<211> LENGTH: 15
<212> TYPE: PRT
<213> ORGANISM: Artificial
<220> FEATURE:
<223> OTHER INFORMATION: Epitope

<400> SEQUENCE: 35

```
Thr Glu Asp Thr Met Thr Lys Leu Arg Glu Leu Ser Glu Leu Ser
1               5                   10                  15
```

<210> SEQ ID NO 36
<211> LENGTH: 9
<212> TYPE: PRT
<213> ORGANISM: Artificial
<220> FEATURE:
<223> OTHER INFORMATION: Epitope

<400> SEQUENCE: 36

```
Ala Leu Gln Pro Gly Thr Ala Leu Leu
1               5
```

<210> SEQ ID NO 37
<211> LENGTH: 9
<212> TYPE: PRT
<213> ORGANISM: Artificial
<220> FEATURE:
<223> OTHER INFORMATION: Epitope

<400> SEQUENCE: 37

```
Ala Ile Leu Ala Leu Leu Pro Ala Leu
1               5
```

<210> SEQ ID NO 38
<211> LENGTH: 9
<212> TYPE: PRT
<213> ORGANISM: Artificial
<220> FEATURE:
<223> OTHER INFORMATION: Epitope

<400> SEQUENCE: 38

```
Ala Leu Leu Met Ala Gly Leu Ala Leu
1               5
```

<210> SEQ ID NO 39
<211> LENGTH: 10
<212> TYPE: PRT
<213> ORGANISM: Artificial
<220> FEATURE:
<223> OTHER INFORMATION: Epitope

<400> SEQUENCE: 39

Leu Leu Cys Tyr Ser Cys Lys Ala Gln Val
1               5                   10

<210> SEQ ID NO 40
<211> LENGTH: 15
<212> TYPE: PRT
<213> ORGANISM: Artificial
<220> FEATURE:
<223> OTHER INFORMATION: Epitope

<400> SEQUENCE: 40

Leu Leu Ala Asn Gly Arg Met Pro Thr Val Leu Gln Cys Val Asn
1               5                   10                  15

<210> SEQ ID NO 41
<211> LENGTH: 15
<212> TYPE: PRT
<213> ORGANISM: Artificial
<220> FEATURE:
<223> OTHER INFORMATION: Epitope

<400> SEQUENCE: 41

Arg Met Pro Thr Val Leu Gln Cys Val Asn Val Ser Val Val Ser
1               5                   10                  15

<210> SEQ ID NO 42
<211> LENGTH: 15
<212> TYPE: PRT
<213> ORGANISM: Artificial
<220> FEATURE:
<223> OTHER INFORMATION: Epitope

<400> SEQUENCE: 42

Ser Val Ser Glu Ser Asp Thr Ile Arg Ser Ile Ser Ile Ala Ser
1               5                   10                  15

<210> SEQ ID NO 43
<211> LENGTH: 9
<212> TYPE: PRT
<213> ORGANISM: Artificial
<220> FEATURE:
<223> OTHER INFORMATION: Epitope

<400> SEQUENCE: 43

Tyr Leu Glu Tyr Arg Gln Val Pro Gly
1               5

<210> SEQ ID NO 44
<211> LENGTH: 9
<212> TYPE: PRT
<213> ORGANISM: Artificial
<220> FEATURE:
<223> OTHER INFORMATION: Epitope

<400> SEQUENCE: 44

Glu Gly Asp Cys Ala Pro Glu Glu Lys
1               5

<210> SEQ ID NO 45
<211> LENGTH: 5
<212> TYPE: PRT
<213> ORGANISM: Artificial
<220> FEATURE:
<223> OTHER INFORMATION: Linker ((Gly4Ser)n

<400> SEQUENCE: 45

Gly Gly Gly Gly Ser 1               5

<210> SEQ ID NO 46
<211> LENGTH: 6
<212> TYPE: PRT
<213> ORGANISM: Artificial
<220> FEATURE:
<223> OTHER INFORMATION: Linker (GSTSGS)n

<400> SEQUENCE: 46

Gly Ser Thr Ser Gly Ser
1               5

<210> SEQ ID NO 47
<211> LENGTH: 18
<212> TYPE: PRT
<213> ORGANISM: Artificial
<220> FEATURE:
<223> OTHER INFORMATION: Linker

<400> SEQUENCE: 47

Gly Ser Thr Ser Gly Ser Gly Lys Pro Gly Ser Gly Glu Gly Ser Thr
1               5                   10                  15

Lys Gly

<210> SEQ ID NO 48
<211> LENGTH: 23
<212> TYPE: PRT
<213> ORGANISM: Artificial
<220> FEATURE:
<223> OTHER INFORMATION: Linker

<400> SEQUENCE: 48

Glu Phe Ala Lys Thr Thr Ala Pro Ser Val Tyr Pro Leu Ala Pro Val
1               5                   10                  15

Leu Glu Ser Ser Gly Ser Gly
            20

<210> SEQ ID NO 49
<211> LENGTH: 10
<212> TYPE: PRT
<213> ORGANISM: Artificial
<220> FEATURE:
<223> OTHER INFORMATION: Linker

<400> SEQUENCE: 49

Glu Pro Lys Ser Cys Asp Lys Thr His Thr
1               5                   10

<210> SEQ ID NO 50
<211> LENGTH: 12
<212> TYPE: PRT
<213> ORGANISM: Artificial
<220> FEATURE:
<223> OTHER INFORMATION: Linker

<400> SEQUENCE: 50

Glu Leu Lys Thr Pro Leu Gly Asp Thr Thr His Thr
1               5                   10

<210> SEQ ID NO 51
<211> LENGTH: 7
<212> TYPE: PRT
<213> ORGANISM: Artificial
<220> FEATURE:
<223> OTHER INFORMATION: Linker -continued

<400> SEQUENCE: 51

Glu Ser Lys Tyr Gly Pro Pro
1               5

MULTI-SPECIFIC BINDING MOLECULES TARGETING ABERRANT CELLS

CROSS-REFERENCE TO RELATED APPLICATIONS

This application is a national phase entry under 35 U.S.C. § 371 of International Patent Application PCT/NL2012/050675, filed Sep. 26, 2012, designating the United States of America and published in English as International Patent Publication WO2013/048243 A1 on Apr. 4, 2013, which claims the benefit under Article 8 of the Patent Cooperation Treaty to U.S. Application Ser. No. 61/540,920, filed Sep. 29, 2011.

TECHNICAL FIELD

The disclosure relates to the field of antibody-like molecules targeted at aberrant cells in autoimmune diseases and cancers. The disclosure also relates to such proteinaceous molecules targeting aberrant cells, while leaving normal cells essentially unaffected. More in particular, the disclosure relates to (single-chain) proteinaceous molecules comprising binding domains specific for at least two different binding sites on aberrant cells.

BACKGROUND

The major challenge for today's drug discovery community is the design of therapeutic molecules that are sufficiently specific for aberrant cells related to malignancies, such as cancers and autoimmune diseases. Such specificity is required to attain acceptable low drug-related adverse reactions for healthy cells. The major hurdle to overcome is the presence of target molecules, not only on/at aberrant cells, but also on healthy cells, albeit at lower frequency. Truly tumor-specific targets or aberrant cell-specific targets are very rare.

DISCLOSURE

Provided are proteinaceous binding molecules with improved specificity for targeting aberrant cells, accompanied by a reduced risk for unwanted side effects induced by unintentionally targeting normal cells.

Thus, provided is a proteinaceous molecule comprising at least two different specific binding domains for different binding sites separated by at least one linker, wherein the proteinaceous molecule comprises a single polypeptide chain.

As used herein, "proteinaceous molecules" are molecules comprising at least a string of amino acid residues that can be obtained as an expression product from a single messenger RNA molecule. In addition, according to the disclosure, the proteinaceous molecules may comprise carbohydrates, disulphide bonds, phosphorylations, sulphatations, etc., as a result of any post-translational modification, and/or any other modification such as those resulting from chemical modifications (e.g., linking of effector moieties). In one embodiment, the proteinaceous molecules comprise a single polypeptide chain comprising at least two specific binding domains. In a preferred embodiment, the proteinaceous molecules of the disclosure comprise binding domains separated by at least one linker. Of course, the proteinaceous molecules of the disclosure can also comprise other functionalities, for example, provided with protein domains or amino acid sequences, linked through peptide bonds or through any linker chemistry known in the art.

A "polypeptide chain" is defined as a string of amino acid residues. "Specific binding domains" are domains that preferentially bind to binding sites on molecules, such as epitopes, with a higher binding affinity than background interactions between molecules. In the context of the disclosure, "background interactions" are interactions with an affinity lower than a $K_D$ of 10E-4 M. Preferably, specific binding domains bind with an affinity higher than a $K_D$ of about 10E-5 M. Specific binding domains in the proteinaceous molecules of the disclosure have at least a molecular size allowing their folding into a binding site. At the upper size limit, the binding domains have a size still allowing proper and stable folding and expression. Typically, domains meeting these size requirements are approximately 25 up to 500 amino acid residues in length, and preferred domains are 40 to 200 amino acid residues in length, and, more preferably, domains are about the size of a variable domain of a heavy chain of an immunoglobulin ("Vh"). For the proteinaceous molecules of the disclosure, of particular use are specific binding domains present in immune molecules, such as those present in T-cell receptors and immunoglobulins. Especially, a Vh sequence is a preferred specific binding domain in the proteinaceous molecules of the disclosure. Vh domains are especially suitable for use as a specific binding domain. Vh domains are relatively stable and easy to obtain via various expression systems. Moreover, engineering methods to further improve, for example, domain stability or solubility are readily available. An available good source for such binding domains consisting of Vh sequences are phage display libraries. Also, a good source for such binding domains are natural libraries, synthetic libraries and semi-synthetic libraries.

As said, the specific binding domains in the proteinaceous molecules of the disclosure are separated by at least one linker. Preferably, these linkers are connected with binding domains through peptide bonds. In many instances, a simple Gly-Ser linker of 4-15 amino-acid residues may suffice, but if greater flexibility of the amino-acid chain is desired and/or when greater spacing between consecutive domains is desired, longer or more complex linkers may be used. Preferred linkers are (Gly$_4$Ser)$_n$(SEQ ID. NO:11), (GlySer-ThrSerGlySer)$_n$ (SEQ ID. NO:12) or any other linker that provides flexibility for protein folding and flexibility for the polypeptide to exhibit its dual or multiple activity, i.e., binding to two or more different binding sites. Additional examples of suitable linkers are the linker sequences connecting domains in human multi-domain plasma proteins. Using linker sequences adapted from multi-domain plasma proteins including immunoglobulins has several advantages. Use of these human amino-acid sequences that are exposed in plasma in the molecules of the disclosure may lower the risk for adverse immune responses. Moreover, these linker sequences are optimized by natural selection to provide multi-domain proteins required inter-domain flexibility for exerting several protein-target interactions simultaneously, involving two or more domains in the multi-domain protein. Examples of such multi-domain plasma proteins comprising inter-domain linkers are vitronectin, fibrinogen, factor VIII, fibronectin, von Willebrand factor, factor XII, plasminogen, factor H, factor I, C1, C3, beta2-glycoprotein 1, immunoglobulin M, and immunoglobulin G. Examples of linkers particularly suitable for covalently connecting domains in the single-chain molecules of the disclosure are linkers based on amino-acid sequences of hinge regions in immunoglobulins of preferably human origin.

According to the disclosure, the at least two specific binding domains of the proteinaceous molecules of the disclosure are different binding domains, endowed with binding affinity for at least two different binding sites. It is appreciated that within the context of the current disclosure, binding sites are (parts of) molecules associated with the cell surface of aberrant cells. It is part of the disclosure that the different binding sites are part of different molecules, or are located on the same molecule, or any combination thereof. Thus, according to the disclosure, the at least two different binding sites targeted by the at least two different specific binding domains of the proteinaceous molecules of the disclosure are associated with the cell surface of aberrant cells. In a preferred embodiment of the disclosure, the different binding sites are co-located at the surface of the same aberrant cell. Preferred binding sites are binding sites located at aberrant cell surface molecules. Examples of such cell surface molecules are integrins, cell surface receptors, cell surface markers, and major histocompatibility complex molecules complexed with T-cell epitopes.

An "aberrant cell" is defined as a cell that deviates from its healthy normal counterparts. Aberrant cells are, for example, tumor cells and autoimmune cells.

Thus, according to the disclosure, proteinaceous molecules comprising at least two different specific binding domains are provided ("multi-specific" proteinaceous molecules) that are particularly suitable for binding to at least two different binding sites associated with the cell surface of aberrant cells. By targeting with a single binding molecule two or more target binding sites on an aberrant cell such as a tumor cell, the risk that both targets are also present on one healthy cell is significantly diminished. The affinity of the binding molecules for the different target binding sites separately, preferably is designed such that Kon and Koff are very much skewed towards binding with all different binding sites simultaneously. Preferably, normal cells having only one of the different target binding sites are not bound for a time long enough, if at all, thereby reducing the occurrence of any deleterious effects. Thus, the specificity of the proteinaceous molecules of the disclosure is increased by increasing their avidity for binding to multiple binding sites on aberrant cells. The avidity is preferably increased by incorporating multiple copies, preferably two to six copies, of at least one of the at least two different binding domains in the proteinaceous molecules ("multi-valent" proteinaceous molecules). FIGS. 1 and 2 give a number of possible preferred molecular designs. It is appreciated that at least one copy of each of the at least two different specific binding domains of the proteinaceous molecules of the disclosure must bind to their respective binding sites. Of course, it is preferred that two or more of the copies bind simultaneously, and most preferably, all copies of a binding domain present in the proteinaceous molecule bind simultaneously.

In an additional embodiment of the disclosure, a proteinaceous molecule is provided, comprising at least three specific binding domains for different binding sites separated from each other by at least one linker.

It is preferred that proteinaceous molecules of the disclosure comprise the minimal number of different specific binding domains providing the specificity for aberrant cells over normal cells. It is then also preferred that the proteinaceous molecules of the disclosure comprise the minimal number of copies of each of the different specific binding domains required for providing the desired specificity. These optimal proteinaceous molecules of the disclosure regarding specificity are selected from possible proteinaceous molecules with varying numbers of different binding domains, varying numbers of copies of each of the different domains, and different domain topologies possible with the varying numbers of different domains and copies. Preferably, proteinaceous molecules of the disclosure comprise two or three different binding domains. Preferably, proteinaceous molecules of the disclosure comprise one to six copies of each of the different domains. Thus, a typical proteinaceous molecule of the disclosure comprises two different binding domains A, B with four copies of each domain, with domain topology A-B-A-B-A-B-A-B. See FIGS. 1 and 2 for some typical examples of preferred proteinaceous molecules regarding number of different domains, copies of domains and topologies.

Repetitive proteinaceous structures are sometimes difficult to express. By selecting (modestly) different binding domains specific for the same molecule, or even for the same binding site on the molecule, expression issues with repetitive structures are largely diminished. These expression problems are further addressed by selecting different linkers for connecting consecutive domains. Thus, an example of a typically preferred molecule of the disclosure has the following structure: A-linker1-B'-linker2-A"-linker3-B-linker1-A'-linker2-B".

Thus, according to the disclosure, proteinaceous molecules comprising at least three different specific binding domains are provided that are particularly suitable for binding to at least three different binding sites associated with the cell surface of aberrant cells. In a preferred embodiment, the proteinaceous molecules of the disclosure comprise specific binding domains comprising at least one Vh domain. More preferably, all two, three or more specific binding domains in the proteinaceous molecules of the disclosure are Vh domains. Thus, a proteinaceous molecule, according to the disclosure, is a proteinaceous molecule wherein at least one specific binding domain is a Vh domain. Preferably, Vh domains are human Vh domains.

As said, in a preferred embodiment of the disclosure, the different binding sites targeted by the proteinaceous molecules of the disclosure are located at the surface of the same aberrant cell. It is preferred that the molecules comprising the binding sites are internalized into the tumor cell together with the binding molecule of the disclosure. In a preferred embodiment, the cells go into apoptosis as a result of internalization. Also incorporated in the disclosure are proteinaceous molecules that, upon binding to target aberrant cells, mediate target aberrant cell lysis or phagocytosis. Thus, the disclosure provides a proteinaceous molecule wherein at least one binding domain is a ligand for a receptor, or a receptor binding fragment and/or derivative of such a ligand. It is preferred that binding of such binding domains to the target receptor on the tumor cell induces internalization of the bound proteinaceous molecules of the disclosure. Preferred suitable ligands for receptors are growth factors, lectins, kinases, hormones, cytokines, chemokines, Toll-like receptor ligands and T-cell epitopes, to name a few.

In one preferred embodiment, the proteinaceous molecules of the disclosure further comprise at least one effector moiety, linked to the polypeptide chain comprising the specific binding domains. Effector moieties preferably improve the potency of a therapeutic molecule and/or increase the efficacy of a therapeutic molecule. It is part of the current disclosure that effector moieties are covalently bound to proteinaceous molecules of the disclosure via peptide bonds, and preferably via a linker. Alternatively, as part of the disclosure, effector moieties are linked to the proteinaceous molecules applying any other suitable linker chemistry known in the art. Yet in another embodiment, the proteinaceous molecules of the disclosure comprise specific binding domains for binding sites on effector moieties. An advantage of such binding molecules of the disclosure is the provided flexibility in the order of binding events. Proteinaceous molecules of the disclosure can first bind to target binding sites on aberrant cells, followed by binding to an effector moiety exposed to the proteinaceous molecules localized on the aberrant cells. Such a proteinaceous molecule of the disclosure is, for example, used for the treatment of cancer. An advantage of such proteinaceous molecules is the possibility of specific delivery of the effector moiety at aberrant cells, preventing normal cells from being exposed to the deleterious effects of the effector moiety.

Preferred effector moieties, according to the disclosure, are numerous, e.g., toxins, statins, apoptin, chelated radioactive metal ions, and radioactive iodine. Other suitable effector moieties, according to the disclosure, are ricin A, gelonin, saporin, interleukin-2, interleukin-12, viral proteins E4orf4 and NS1, and non-viral cellular proteins HAMLET, TRAIL and mda-7 of which the latter five can, like apoptin, specifically induce apoptosis in aberrant cells after internalization of the proteinaceous molecules of the disclosure comprising at least one of such effector moieties.

When proteinaceous molecules of the disclosure are designed to first bind to a target aberrant cell, followed by internalization, the effector moiety can then subsequently have its intracellular (cytotoxic) function. It is preferred that such an effector moiety has a contribution to the specificity of the cytotoxic effect. Therefore, it is preferred to use as an effector moiety a molecule that induces cell death in aberrant cells, but not in normal cells. An example of such a specific effector moiety is apoptin.

Thus, the disclosure provides a proteinaceous molecule, further comprising an effector moiety.

As said, preferred proteinaceous molecules of the disclosure comprise at least two different specific binding domains. Particularly suitable and preferred specific binding domains are domains based on Vh sequences. Thus, the disclosure also provides a proteinaceous molecule comprising at least two Vh domains. A few examples of such molecules of the disclosure are provided in FIGS. 1 and 2. In a preferable embodiment, these Vh domains are derived from human Vh sequences. It is appreciated that Vh domains, as such, are already relatively stable. Still, stability and solubility of human Vh domains can be further improved by engineering approaches known in the art. Particularly suitable for the purpose is applying a process referred to as "camelization" of the human Vh sequence. Now, selected amino acid residues in the human Vh sequence, not contributing to the binding specificity and affinity of the domain, are replaced for amino acid residues present at the corresponding sites of llama Vh domains. Preferred amino acid substitutions contributing to improved stability/solubility are Glu6Ala, Ala33Cys, Val37Phe, Gly44Glu, Leu45Arg, Trp47Gly, Ser74Ala, Arg83Lys, Ala84Pro, Trp103Arg or Leu108Gln. Thus, the disclosure also provides a proteinaceous molecule comprising camelized human Vh domains with improved stability and/or solubility.

Other functions that may be introduced in the proteinaceous molecules of the disclosure may have to do with improved half-life (e.g., human serum albumin (HSA) can be included or one or more binding domains binding to a binding site in HSA) or with complement activation (Fc monomer of immunoglobulins can be included; in this case the molecules, according to the disclosure, may dimerize).

Other functionalities that can be incorporated are cytokines, hormones, Toll-like receptor ligands, (activated) complement proteins, etc.

Thus, the disclosure provides a proteinaceous molecule comprising at least two Vh domains specific for different binding sites and an Fc monomer. And, thus, the disclosure also provides a dimeric proteinaceous molecule, comprising two proteinaceous molecules dimerized through two Fc monomers. Proteinaceous molecules comprising immunoglobulin CH3 domains are also part of the disclosure. Similar to Fc monomers, the CH3 domain can serve as a dimerization domain. Homo-dimeric as well as hetero-dimeric proteinaceous molecules are part of the disclosure. Homo-dimeric binding molecules comprise dimerized Fc monomers with identical arms. The heterogeneity of hetero-dimeric proteinaceous molecules of the disclosure originates from the two Fc monomers in the hetero-dimer, differing in the type, number and/or topology of their respective specific binding domains, linkers and/or effector moieties. Thus, in one embodiment, the disclosure provides a hetero-dimeric molecule comprising two different proteinaceous molecules. The two different proteinaceous molecules are then dimerized through their respective Fc monomers. Upon applying preferred pairing biochemistry, hetero-dimers are preferentially formed over homo-dimers. For example, two different Fc monomers are subject to forced pairing upon applying the "knobs-into-holes" CH3 domain engineering technology as described (Ridgway et al., *Protein Engineering*, 1996). An advantage of the proteinaceous molecules of the disclosure comprising dimerized Fc monomers is the localization of phagocytosis and/or cell lytic activity at the surface of aberrant cells to which these proteinaceous molecules bind. These activities can enhance the deleterious effects on aberrant cells, induced by the proteinaceous molecules of the disclosure specifically bound to these aberrant cells. An advantage of such hetero-dimeric proteinaceous molecules of the disclosure is their increased spatial flexibility regarding the different/differently located specific binding domains in the two arms.

In one embodiment, binding molecules are provided comprising one or multiple copies of each of at least two different binding domains specific for at least two different binding sites on aberrant cells. Cellular aberrancies, such as cancers and autoimmune diseases, are manifested by the presence of unique combinations of surface molecules on the aberrant cell surface and/or by the relatively high cell-surface density of the surface molecules. It is thus one of the preferred embodiments that the at least two different binding sites targeted by proteinaceous molecules of the disclosure are located on aberrant cells. It is even more preferred that these at least two different binding sites are not all present on normal cells, and/or are present at lower numbers on normal cells. An example are proteinaceous molecules, according to the disclosure, comprising at least one copy of a specific binding domain for a binding site in carcinoembryonic antigen (CEA) and at least one copy of a specific binding domain for a binding site in MUC-1 with altered glycosylation pattern, expressed in aberrant cells of the colon during colorectal cancer. Altered MUC-1 is not expressed in normal cells of the colon; CEA is over-expressed on tumor cells in the colon. It is thus most preferred that all of the at least two different binding sites are unique to aberrant cells and not present at all on normal cells. Examples of such combinations of binding sites are T-cell epitopes derived from tumor-specific markers, complexed with HLA. Thus, in a preferred embodiment, a proteinaceous molecule, according to the disclosure, is provided for use in the treatment of a disease related to aberrant cells.

For administration to subjects, the proteinaceous molecules, according to the disclosure, must be formulated. Typically, these proteinaceous molecules will be given parentally. For formulation, simply saline for injection may suffice. For stability reasons, more complex formulations may be necessary. The disclosure contemplates lyophilized compositions as well as liquid compositions, provided with the usual additives. Thus, the disclosure provides a pharmaceutical composition comprising a proteinaceous molecule, according to any of the embodiments of the disclosure and suitable excipients.

The dosage of the proteinaceous molecules, according to the disclosure must be established through animal studies and clinical studies in so-called rising-dose experiments. Typically, the doses will be comparable with present-day antibody dosages (at the molar level, the weight of the molecules may differ from that of antibodies). Typically, such dosages are 3 to 15 mg/kg body weight, or 25 to 1000 mg per dose.

It is anticipated that in the field of, for example, tumor therapy, the proteinaceous molecules of the disclosure will replace current single agents binding to a single binding site. In addition, especially in the more difficult to treat tumors, the first applications of the proteinaceous molecules, according to the disclosure, will (at least initially) probably take place in combination with other treatments (standard care). Of course, the disclosure also provides proteinaceous molecules for use in novel or first treatments of any other tumor, for which current treatments are not efficient enough or for which no treatment options are currently available. Thus, the disclosure also provides a pharmaceutical composition comprising a proteinaceous molecule and a conventional cytostatic and/or tumoricidal agent. Moreover, the current disclosure also provides a pharmaceutical composition comprising a proteinaceous molecule for use in an adjuvant treatment of cancer. Additionally, the current disclosure also provides a pharmaceutical composition comprising a proteinaceous molecule for use in a combination chemotherapy treatment of cancer. Examples of chemotherapeutical treatments that are combined with the pharmaceutical composition of the current disclosure are etoposide, paclitaxel, doxorubicin and methotrexate.

The pharmaceutical compositions, according to the disclosure, will typically find their use in the treatment of cancer, particularly in forms of cancer where the at least two different binding sites of the preferred proteinaceous molecules of the disclosure are present on tumor cells. It is easy using binding domains, according to the disclosure, to identify tumors that present tumor-specific antigen(s). This can be done in vitro or in vivo (imaging).

The disclosure, of course, also comprises a nucleic acid molecule encoding a proteinaceous molecule according to any of the embodiments of the disclosure. The molecules, according to the disclosure, can be produced in prokaryotes as well as eukaryotes. The codon usage of prokaryotes may be different from that in eukaryotes. The nucleic acids, according to the disclosure, can be adapted in these respects. Also, elements that are necessary for secretion may be added, as well as promoters, terminators, enhancers, etc. Also, elements that are necessary and/or beneficial for the isolation and/or purification of the proteinaceous molecules may be added. Typically, the nucleic acids, according to the disclosure, are provided in an expression vector suitable for the host in which they are to be produced. Choice of a production platform will depend on the size of the molecule, the expected issues around protein folding, whether additional sequences are present that require glycosylation, expected issues around isolation and/or purification, etc. For example, whether or not specific binding domains of the disclosure comprise disulphide bonds will guide the selection of the preferred production platform. Thus, nucleic acids, according to the disclosure, are typically adapted to the production and purification platform in which the proteinaceous molecules, according to the disclosure, are to be produced. Thus, the disclosure provides a vector comprising a nucleic acid molecule encoding a proteinaceous molecule, according to the disclosure. For stable expression in a eukaryote, it is preferred that the nucleic acid encoding the proteinaceous molecule, according to the disclosure, is integrated in the host cell genome (at a suitable site that is not silenced).

In one embodiment, the disclosure, therefore, comprises a vector comprising means for integrating the nucleic acid in the genome of a host cell. The disclosure further comprises the host cell or the organism in which the proteinaceous molecule encoding nucleic acid molecule is present and which is thus capable of producing the proteinaceous molecule, according to the disclosure. Thus, in a preferred embodiment, the disclosure comprises a cell comprising a nucleic acid molecule, according to the disclosure, preferably integrated in its genome and/or a vector, according to the disclosure, comprising a nucleic acid molecule encoding a proteinaceous molecule, according to the disclosure.

Included in the present disclosure is also a method for producing a proteinaceous molecule, according to the disclosure, comprising culturing a cell, according to the disclosure, comprising a nucleic acid molecule encoding a proteinaceous molecule, according to the disclosure, preferably integrated in the cell's genome and/or a vector, according to the disclosure, comprising a nucleic acid molecule encoding a proteinaceous molecule, according to the disclosure, allowing for expression of the proteinaceous molecule and separating the proteinaceous molecule from the culture.

Typical proteinaceous molecules of the disclosure, according to any of the aforementioned embodiments, are provided and exemplified by the binding molecules outlined in this section, in FIG. 1 and FIG. 2, and by the examples provided below and in the Examples section. Thus, the disclosure provides a proteinaceous molecule, according to FIG. 1 or FIG. 2.

Abbreviations used: Ab, antibody; ADCC, antibody-dependent cell-mediated cytotoxicity; CDC, complement-dependent cytotoxicity; CDR, complementarity-determining region; CH, constant domain of the heavy chain of an antibody; CHO, Chinese hamster ovary; DAMPs, damage associated molecular patterns; HEK, human embryonic kidney; IEP, iso-electric point; Ig, immunoglobulin; MAGE, melanoma-associated antigen; MHC, major histocompatibility complex; PAMPs, pathogen associated molecular patterns; RA, rheumatoid arthritis; sc-Fv, single-chain variable fragment; SLE, systemic lupus erythematosis; $V_{HH}$ or sdAb, single domain antibodies; TCR, T-cell receptor; VH, Vh or $V_H$, variable amino-acid sequence of an antibody heavy domain.

BRIEF DESCRIPTION OF THE DRAWINGS

FIG. 1: Exemplified topologies of binding molecules comprising one or more copies each of two or more different binding domains, each binding to a different binding site, according to the disclosure, and in one embodiment comprising effector moieties as part of the disclosure.

Figure 2:
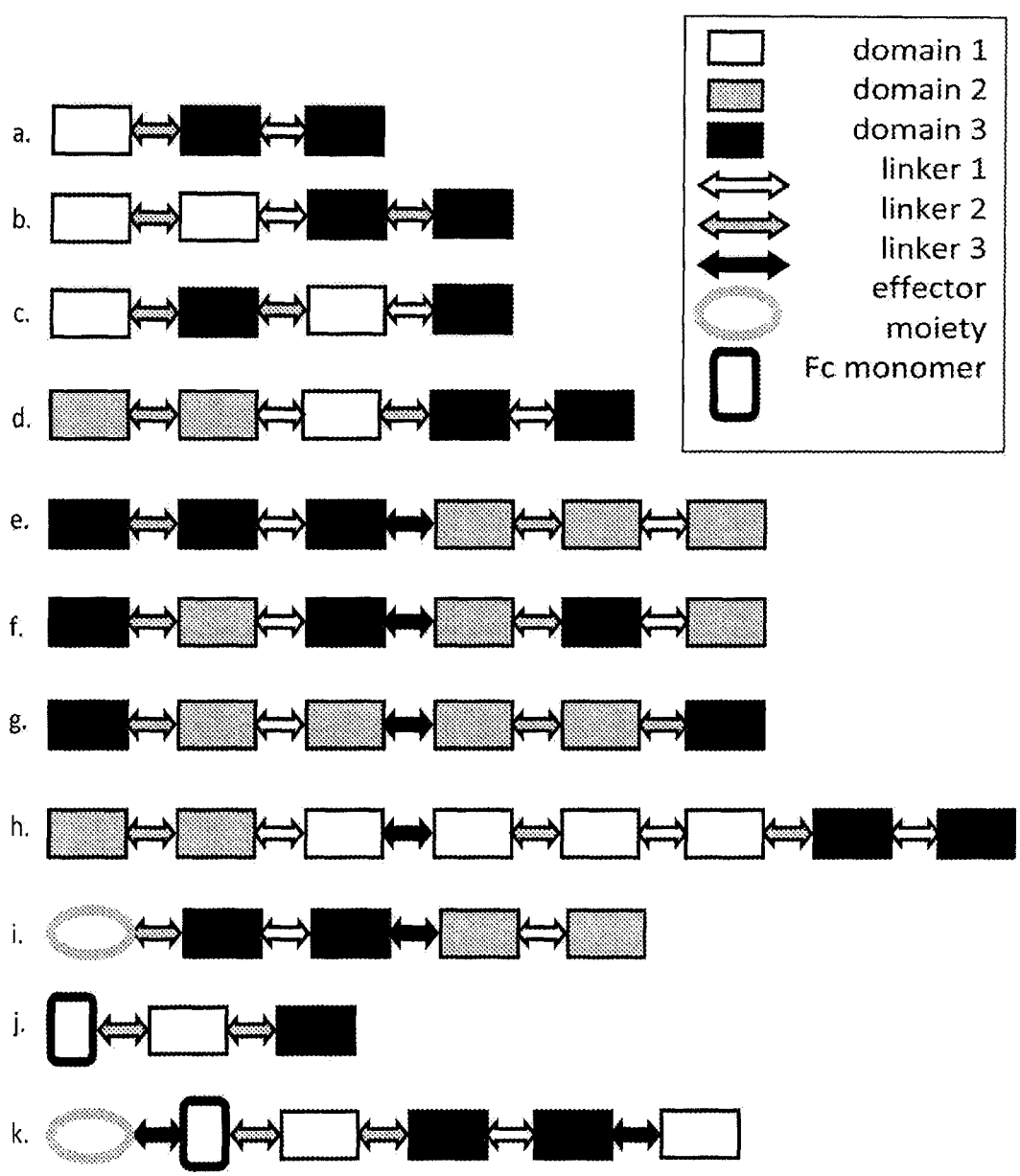

1. Topologies of binding molecule comprising two different binding domains "D1" and "D2," and divalent for a binding site 1 and monovalent for a binding site 2.

2. Binding molecule comprising two different binding domains and monovalent for a binding site 1 and multivalent for a binding site 2 (multi-valency is, for example, three to six). Shown are two examples of many possible single-chain polypeptides according to the disclosure. All possible permutations regarding the position of the single binding domain and the multiple copies of the second binding domain are also part of the disclosure, and are visualized by the ensemble of different domains and number of domains between accolades.

3. Binding molecule comprising two different binding domains, each binding to a different binding site and with two to six copies of a first binding domain and with two to six copies of a second binding domain, providing multi-valency for both binding sites. As an example, a binding molecule is shown in which binding domains binding to the same binding site are linked in consecutive order. All possible domain topologies obtained by permutations regarding domain positions in the single chain binding molecule of all binding domains of both kinds, are also part of the disclosure.

4. Binding molecule comprising three, four, five or six different binding domains, thus binding to three, four, five or six different binding sites, respectively, and monovalent or multivalent for a binding site 1, monovalent or multivalent for a binding site 2, etc., (the valencies for the three to six different binding sites are, for example, one to six). As an example, four binding molecules are shown in which one to six clustered identical binding domains are linked in consecutive order, with three, four, five and six different binding domains in the binding molecules, respectively. All possible domain topologies obtainable by permutations regarding domain positions in the single chain binding molecule, of all one to six copies of the three to six different binding domains, are also part of the disclosure.

5. Binding molecule comprising two different binding domains, each binding to a separate binding site and with one binding domain monovalent or multivalent for a binding site 1 and the second binding domain monovalent or multivalent for a binding site 2 (both valencies are, for example, one to six), and with one or more effector moieties (covalently) bound to the binding molecule. As an example, a binding molecule is shown in which the two sets of one to six binding domains are linked in consecutive order, with the effector moiety covalently linked to the C-terminus of the binding molecule. All possible domain topologies obtainable by permutations regarding each domain position in the single chain binding molecule are also part of the disclosure.

6. Similar to 5, now with three to six different binding domains, for each of which, one to six copies of the unique binding domains are part of the binding molecule.

FIG. 2: Cartoon displaying examples of preferred domain topologies of proteinaceous molecules of the disclosure. Examples are provided of possible combinations of $V_H$ domains and distinct linker sequences for the construction of multi-domain proteins that are multi-specific. In Lanes a through h, various examples are provided of proteinaceous molecules of the disclosure, comprising two or three different binding domains, and comprising one, two, three or four copies of the various binding domains, each, all linked with two or three different linkers (see, also, FIG. 1, example 1 through 4, for additional preferred domain topologies of the disclosure). In Lanes i and k, the exemplified preferred proteinaceous molecules of the disclosure further comprise an effector moiety linked to the single-chain polypeptide comprising different binding domains (additional preferred proteinaceous molecules of the disclosure comprising at least one effector moiety are provided in examples 5 and 6 in FIG. 1). In Lanes j and k, the exemplified preferred proteinaceous molecules of the disclosure further comprise an Fc monomer linked to the different binding domains.

Figure 3:
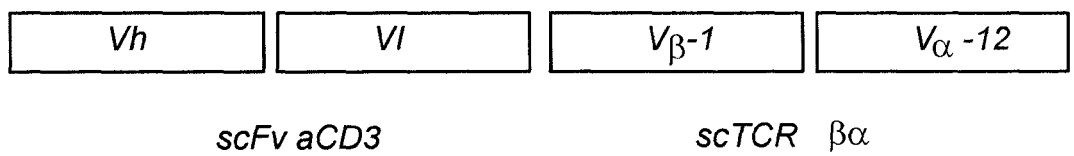

FIG. 3: is a schematic presentation of the bispecific scFv anti-CD3×scTCR ßα with HLA-A1/MAGE-A1 specificity.

Figure 4:
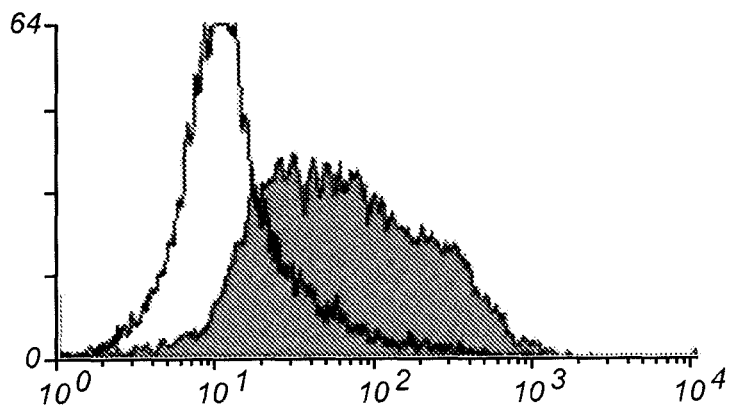

FIG. 4: shows the binding of the bispecific scFv anti-CD3×scTCR ßα to primary human T-lymphocytes. Binding of the bispecific scFv anti-CD3×scTCR ßα to primary human T-lymphocytes was verified by flow-cytometry using FITC-labelled anti-Vα-12.1 specific mAb. In short, $0.5 \times 10^6$ primary human T-lymphocytes were incubated for 30 minutes (on ice) with supernatant from 293T cells expressing the bispecific scFv×scTCR. Next, 1 μg FITC-labelled anti-Vα-12.1 was added and incubated for 30 minutes. Shown are cells bound by the bispecific scFv×scTCR stained with an irrelevant FITC labelled antibody (negative control; white) and cells bound by the scFv×scTCR labelled with Vα-12.1.

Figure 5:
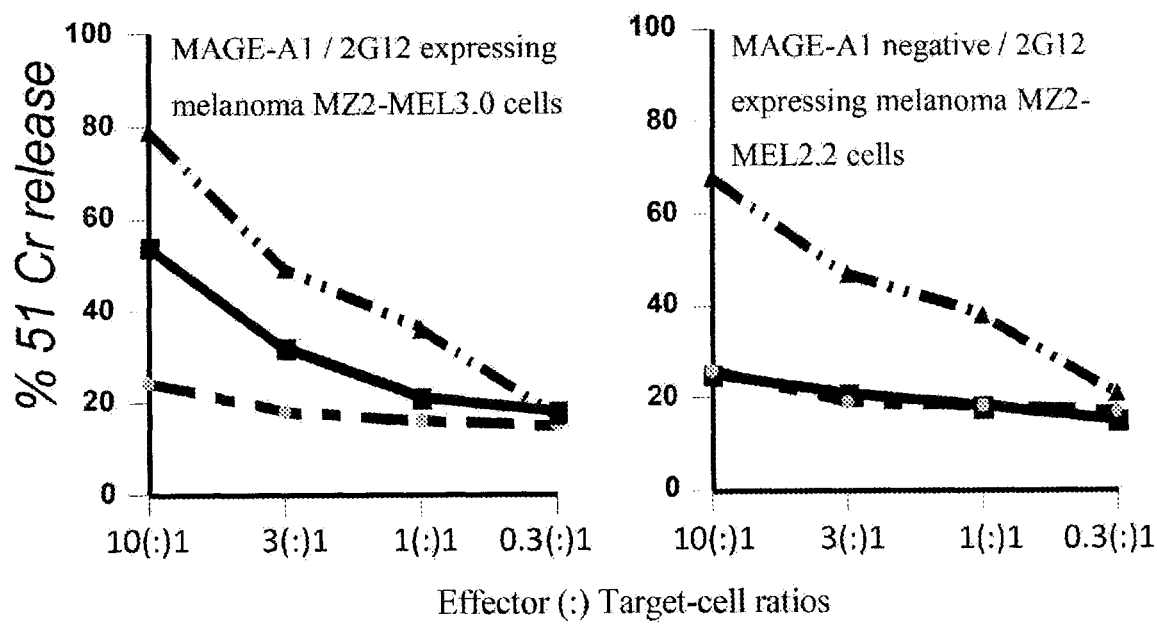

FIG. 5: shows that primary human T-lymphocytes specifically kill HLA-A1/MAGE-A1 positive tumor cells. X-axis: Effector (:) Target-cell ratios 10(:)1, 3(:)1, 1(:)1, 0.3(:)1. The _.. _ .. _ line depicts T-lymphocytes with melanoma cell-specific antigen 2G12-specific bispecific molecule, the straight line (-) depicts T-lymphocytes plus HLA-A1-MAGE-A1 specific bispecific molecule, the - - - - line depicts T-lymphocytes without bispecific molecule. Primary human T-lymphocytes were labelled with either the HLA-A1/MAGE-A1 bispecific scFv×scTCR or with an 2G12 antigen specific scFv×scFv. These T-lymphocytes were incubated for 4 hours with 51Cr labelled HLA-A1/MAGE-A1, and 2G12 antigen-positive melanoma cells MZ2 MEL3.0. As a negative control MZ2 –MEL 2.2 cells that have lost expression of MAGE-A1, but still have 2G12 expression, were used. As shown, the 51 Cr-release assay demonstrates specific tumor cell kill by scFv×scTCR labelled human T-lymphocytes.

DETAILED DESCRIPTION

A further aspect of the disclosure relates to a method for providing the binding molecules, according to the disclosure. As described hereinabove, it typically involves providing a nucleic acid construct encoding the desired binding molecule. The nucleic acid construct can be introduced, preferably via a plasmid or expression vector, into a prokaryotic host cell and/or in a plant cell and/or in a eukaryotic host cell capable of expressing the construct. In one embodiment, a method of the disclosure to provide a binding molecule comprises the steps of providing a host cell with one or more nucleic acid(s) encoding the binding molecule, and allowing the expression of the nucleic acids by the host cell.

Binding molecules of the disclosure are, for example, expressed in plant cells, eukaryotic cells or in prokaryotic cells. Non-limited examples of suitable expression systems are tobacco plants, *Pichia pastoris, Saccharomyces cerevisiae*. Also, cell-free recombinant protein production platforms are suitable. Preferred host cells are bacteria, like, for example, bacterial strain BL21 or strain SE1, or mammalian host cells, more preferably, human host cells. Suitable mammalian host cells include human embryonic kidney (HEK-293) cells or Chinese hamster ovary (CHO) cells, which can be commercially obtained. Insect cells, such as S2 or S9 cells, may also be used using baculovirus or insect cell expression vectors, although they are less suitable when the polypeptides, according to the disclosure, include elements that involve glycosylation. The produced binding molecules, according to the disclosure, can be extracted or isolated from the host cell or, if they are secreted, from the culture medium of the host cell. Thus, in one embodiment, a method of the disclosure comprises providing a host cell with one or more nucleic acid(s) encoding the binding molecule, allowing the expression of the nucleic acids by the host cell. In another preferred embodiment, a method of the disclosure comprises providing a host cell with one or more nucleic acid(s) encoding two or more different binding molecules allowing the expression of the nucleic acids by the host cell. For example, in one embodiment, nucleic acids encoding for two or more different binding molecules, all comprising an Fc monomer, are provided, enabling isolation of multiple single-chain binding molecules, and/or enabling isolation of homo-dimers and/or hetero-dimers formed through Fc dimerization. Methods for the recombinant expression of (mammalian) proteins in a (mammalian) host cell are well known in the art.

As will be clear, a binding molecule of the disclosure finds its use in many therapeutic applications and non-therapeutic applications, e.g., diagnostics, or scientific applications. Proteinaceous molecules of the disclosure suitable for diagnostic purposes are of particular use for monitoring the expression levels of molecules exposing binding sites on aberrant cells that are targeted by proteinaceous molecules of the disclosure applied for their therapeutic benefit. In this way, it is monitored, whether the therapy remains efficacious or whether other proteinaceous molecules of the disclosure targeting one or more different binding sites on the aberrant cells should be applied instead. This is beneficial when the expression levels of the first targeted binding site(s) are below a certain threshold, whereas other or new binding sites (still) can serve as newly targeted binding sites for proteinaceous molecules of the disclosure comprising the appropriate specific binding domains for these alternative binding sites. Binding molecules of the disclosure may also be used for the detection of (circulating) tumor cells, for the target cell-specific delivery of cytotoxic compounds or for the delivery of immune-stimulatory molecules.

Provided herein is a method for inducing, ex vivo or in vivo, a modulating effect on a biological process at or in a target cell, comprising contacting the cell with a binding molecule, according to the disclosure, in an amount that is effective to induce the modulating effect. According to the disclosure, the modulating effect or combined modulating effects is/are agonistic, or stimulatory, or activating in nature, or the effect(s) is/are interfering, or antagonistic in nature, or any combination thereof. In addition, the modulating effect(s) is/are additive or synergistic in nature for different binding domains in the binding molecules, or combinations thereof.

Preferably, the binding molecule is used for a modulating effect on a biological process of aberrant cells in a subject, more preferably a human subject. For therapeutic applications in humans, it is, of course, preferred that a binding molecule does not contain amino acid sequences of non-mammalian origin. More preferred are binding molecules that only contain human amino acid sequences. Therefore, a therapeutically effective amount of a binding molecule capable of recognizing and binding to one or more disease-specific binding sites and subsequently inducing a modulating effect on a biological process at the cell surface or in the cell, can be administered to a patient to stimulate eradication of diseased cells expressing the binding sites without affecting the viability of (normal) cells not expressing the disease-specific binding sites. The killing of diseased cells, while minimizing or even totally avoiding the deterioration or even death of normal cells, will generally improve the therapeutic outcome of a patient after administration of the binding molecule.

Accordingly, also provided is the use of a binding molecule, according to the disclosure, as a medicament. In another aspect, the disclosure provides the use of a binding molecule for the manufacture of a medicament for the treatment of cancer, autoimmune disease or any other disease of which the symptoms are reduced upon targeting cells expressing one or more disease-specific binding sites with proteinaceous molecules of the disclosure. For example, a binding molecule is advantageously used for the manufacture of a medicament for the treatment of various cancers (e.g., solid tumors, hematologic malignancies).

Antibody fragments of human origin can be isolated from large antibody repertoires displayed by phages. One aspect of the disclosure, known by the art, is the use of human antibody phage display libraries for the selection of two or more human antibody fragments specific for two or more selected different binding sites, e.g., epitopes. These antibody fragments usually display low affinity. A method is provided that allows the generation of high avidity antibody chains able to bind and exert the modulating biological activity in a specific and efficient manner. An aspect of the present disclosure is the development of a binding molecule comprising multiple binding domains. That is to say, preferably a human Vh domain, capable of binding to a certain binding site combined with a second, third, fourth, and so on, copy of an identical binding domain (multi-valency), and at least one copy of one or more different human Vh domains with each different human Vh domain capable of binding to a separate binding site (multi-specificity). In this way, avidity regarding the first binding site and, if multiple binding domains are applied specific for a second, third, fourth, and so on binding site, avidity regarding this second, third, fourth, and so on binding site is enhanced.

Thus, a proteinaceous molecule is provided comprising at least two copies of a binding domain specific for a binding site functionally connected with at least one copy of a different binding domain specific for a different binding site. Preferably, these different binding domains are functionally connected to each other via peptide bonds between amino acid residues flanking the binding domains, providing a continuous single chain proteinaceous molecule (FIGS. 1 and 2). It is also part of the disclosure that the binding domains are linked together via bonds and/or binding interactions other than peptide bonds. Alternative methods for linking proteinaceous molecules to each other are numerous and well known to those skilled in the art of protein linkage chemistry. Protein linkage chemistry not based on peptide bonds can be based on covalent interactions and/or on non-covalent interactions.

A multi-specific proteinaceous molecule in a mono-valent or multi-valent binding molecule form of the disclosure capable of modulating a biological process is, for example, composed of at least copies of two different human Vh domains, which are multimerized at the DNA level in order to obtain a single-chain polypeptide construct upon expression.

Human Vh domains usually do not meet the standards for stability and efficient expression that are required by the field. They tend to be unstable, poorly soluble and poorly expressed. A process called "camelization" may be used to convert human Vh into more stable antibody fragments.

The human antibody germline region Vh-3 displays high homology with antibody Vh fragments of llamas. Llamas have two types of antibodies, those composed of heavy and light chains, and antibodies that only contain heavy chains. These heavy-chain only antibodies bind antigens similar to classical antibodies composed of heavy and light chains. The smallest functional llama antibody binding domain, the Vhh domain, also called (single) domain antibodies ((s)dAb), have been shown to be expressed well and may bind antigen with high affinity. In addition, it has been shown that some of the characteristics, such as ease of expression and stability, of llama sdAb can be transferred to, e.g., human Vh by replacing a few amino acids in the human Vh for those of llama Vhh. Antibody molecules with multi-specificity can then be generated by ligation of one or more copies of several different "camelized" human Vh domains, each with affinity for different binding sites, into one single molecule. Moreover, high avidity antibody molecules can then be generated by ligation of several of the camelized human Vh domains binding to the same binding site, into one single molecule.

For each of the at least two binding sites, the proteinaceous molecules of the disclosure comprise one to twelve and, more preferably, one to six and, even more preferably, one to three camelized human Vh domains interspersed by short linkers, for example, short Gly-Ser linkers, and connected through peptide bonds to the camelized human Vh domains interspersed by short linkers, specific for the other target binding sites of the binding molecules. In another embodiment, for at least one of the at least two different binding sites, the proteinaceous molecules of the disclosure comprise preferably four to six camelized human Vh domains interspersed by short linkers, herewith providing the molecules with the capacity to cross-link four to six target molecules exposing this targeted binding site. In an even more preferred embodiment, this cross-linking of molecules induces apoptosis in cells expressing surface molecules exposing the targeted binding site for the four to six binding domains.

Compared to binding molecules specific for a single binding site, the proteinaceous molecules of the disclosure have, amongst others, the following advantages regarding efficacy and specificity. The proteinaceous binding molecules of the disclosure have an increased specificity for aberrant cells by targeting multiple binding sites specific for the aberrant cell simultaneously and/or by targeting combinations of binding sites unique to the aberrant cell simultaneously. In this way, aberrant cells are targeted more efficiently, avoiding (excessive) targeting of healthy cells, and thus lowering the risk for toxic and undesired side-effects significantly. This high specificity for aberrant cells is achieved with proteinaceous molecules of the disclosure bearing relatively low affinity for each separate binding site present on aberrant cells and perhaps on healthy cells, while bearing relatively high avidity for aberrant cells exposing a combination of different binding sites unique to the aberrant cells.

Below, several examples are provided for these combinations of binding sites that provide suitable therapeutic targets for the molecules of the disclosure. Moreover, with the multi-specific proteinaceous molecules of the disclosure, difficult to target and/or difficult to reach aberrant cells have a higher chance of being "hit" by at least one of the binding domains, thereby providing, at least in part, the therapeutic activity and increasing the success rate when compared to single molecule/single target therapies. For example, high specificity for aberrant cells is achieved when one or more copies of different binding domains are combined in binding molecules of the disclosure, with the different binding domains individually having relatively low affinity for their respective binding sites, though in combination having relatively high avidity for aberrant cells, either uniquely expressing the combination of binding sites or highly expressing the binding sites relative to healthy cells, or any combination thereof.

Examples of various possible domain topologies in the proteinaceous molecules of the disclosure, as exemplified below, are provided in FIG. 1 and in FIG. 2. In one example, combining two or more different low-affinity binding domains specific for surface markers present on both healthy cells and aberrant cells still provides for proteinaceous molecules of the disclosure highly specific for the aberrant cells, when the surface markers are highly expressed on the aberrant cells, compared to expression levels on healthy cells. Therefore, in a preferred embodiment, the desired high specificity for aberrant cells and concomitant high efficacy regarding aberrant cell eradication, leaving healthy cells in essence unaltered, of the proteinaceous molecules of the disclosure, are tunable ("mix and match" approach) by selecting for, for example:
  (i) optimal target binding sites regarding the level of uniqueness compared to normal cells,
  (ii) optimal number of different binding sites (preferably two or three),
  (iii) optimal number of binding domains for each selected binding site (preferably one to six),
  (iv) optimal domain topologies,
  (v) optimal affinity of each binding domain (preferably larger than a $K_D$ of 10E-5 M),
  (vi) optimal avidity for the proteinaceous,
  (vii) optimal tumor penetration abilities based on molecular size (preferably larger than 65 kDa to reduce glomerular filtration) and iso-electric point (preferably 5-9),
  (viii) optimally facilitating cellular uptake of the proteinaceous molecules of the disclosure (to allow for, for example, pro-apoptotic activity).

In one embodiment, use of the multi-specific proteinaceous molecules of the disclosure now provides for methods to lower the risk for immune escape by aberrant cells. Following current practice, applying a single target binding site therapy bears the risk for unwanted immune escape by the aberrant cell, rendering the therapy ineffective. In general, by natural occurring mutation rates and/or under pressure of a selected (immune) therapy, binding sites on the aberrant cell may eventually mutate. Now alternatively, by targeting two or more different binding sites on the aberrant cell with the proteinaceous molecules of the disclosure, effective binding to at least one or to several binding sites remains, even after occurrence of mutations in one or several of the other binding sites targeted by the proteinaceous molecules of the disclosure. In this way, at least part of the desired therapeutic effect is maintained. This improved therapeutic efficacy over existing therapies under development or on the market is one of the many advantages provided by the embodiments of the current disclosure.

Cells or molecules in a patient that express or expose danger signals are efficiently targeted by binding molecules, according to the disclosure, that are multi-specific, either in a monovalent manner or in a multivalent manner or in any combination thereof, for several damage associated molecular patterns (DAMPs) and/or for several binding sites on one or more DAMPs. DAMPs are, for example, exposed upon ischemia and inflammation and, for example, by aberrant cells such as cancer cells. It is part of the disclosure that the multi-specific binding molecules of the disclosure have the capacity to cross-link cellular proteins, with subsequent induction of biological processes upon activation of pathways mediated by these cross-linked proteins. Examples of such pathways are Fc receptor mediated processes such as Fc receptor mediated uptake of complexes comprising Fc fragments and bound molecules, and the complement pathway(s) of the immune system. Another example is the cross-linking of CD30 on Hodgkin's lymphoma cells by a proteinaceous molecule of the disclosure binding to multiple binding sites on CD30 overexpressed by Hodgkin/Reed-Stenberg cells. Cross-linking of CD30 results amongst others in pro-apoptotic signaling and in anti-proliferative signaling in the aberrant cells. Targeting and inducing clustering of MHC 1-MAGE 1 peptide complex on melanoma cells by proteinaceous molecules of the disclosure comprising at least four, and preferably four to six domains specific for the MHC 1-MAGE 1 peptide complex, induces apoptosis of the targeted aberrant cells. Increased specificity and efficacy of these molecules of the disclosure is, for example, achieved by introducing one or more low-affinity binding domains specific for an epitope on the MHC 1 molecule.

A class of molecules specifically suitable for targeting by the proteinaceous molecules of the disclosure are cellular receptors and their ligands and (proteinaceous) binding partners. Examples of cellular receptors and their ligands are the class of G-protein coupled receptors (GPCRs) and, for example, hormones and neurotransmitters. GPCRs play a role in amongst others cancer. GPCRs act in an activated monomeric form and/or GPCRs act in an activated homodimer or heterodimer GPCRs active as higher order multimers exist as well. It is clear that GPCR homomers and heteromers can have different activities and roles in, for example, disease processes compared to the same GPCR in monomeric form. This provides several ways for intervening in the GPCR mediated biological processes during disease and disorders by binding molecules of the disclosure. By targeting GPCR monomers, and/or homomers, and/or heteromers, and/or GPCR ligands, and/or GPCR-ligand interactions by binding molecules of the disclosure, biological processes contributing to a certain disease can be modulated in a specific and efficient manner. For example, a binding molecule of the disclosure with an agonistic effect comprises two different binding domains binding to the two different GPCRs forming an active GPCR heterodimer, thereby facilitating the complex formation. Alternatively, blocking binding molecules are designed, according to the disclosure, preventing GPCR dimer formation, and thereby GPCR dimer-mediated activation. In general, it is part of the disclosure that any receptor mosaic is targeted in either an inhibitory, or stimulatory fashion by binding molecules of the disclosure. It is appreciated that intervening in receptor-receptor contacts is preferably addressed at the extracellular site of cells.

It is part of the disclosure that the binding molecules act as allosteric molecules and/or as orthosteric ligand molecules for monomeric receptors, homomers, or heteromers, by targeting one or more allosteric binding sites and/or one or more ligand binding sites on the receptors, simultaneously. These binding sites are then located on the same receptor molecule or on different receptor molecules. The binding molecules of the disclosure can also have agonistic activity, synergistic activity and/or co-stimulatory activity. Of course, inhibiting allosteric effects resulting, for example, in receptor oligomerization as part of their activation, is also established by yet different binding molecules of the disclosure, that prevent binding of ligands with an allosteric effect to their binding sites on the receptors.

EXAMPLES

Examples of multiple (preferably two or three) different binding sites each targeted in a monovalent or multivalent (preferably divalent to hexavalent, and even more preferably di-/tri-/tetravalent) manner by proteinaceous molecules of the disclosure comprising at least two different specific binding domains, such as depicted in FIG. 1 and FIG. 2, are provided in the specification and in the Examples 1-5, below.

Example 1

Non-exhaustive examples of proteinaceous molecules of the disclosure comprising binding domains binding to at least two different binding sites which are each targeted in a monovalent or multivalent manner by the two or more different binding domains, with binding domain topologies as outlined, for example, in FIG. 1 and FIG. 2, are:

Proteinaceous molecules of the disclosure comprising binding domains binding to:

1. one or two epitopes in altered MUG-1 and to one or two epitopes in epithelial tumor antigen and/or to one or two epitopes in carcinoembryonic antigen (CEA) and/or to one or two epitopes in ErbB2 and/or to one or two epitopes in Le(y) hapten, for the targeting of aberrant cells in, for example, breast cancer;

2. one or two epitopes in altered MUC-1 and to one or two epitopes in CEA, with one to three copies of the two to four different specific binding domains, for the treatment of gastrointestinal malignancies such as pancreatic cancer, gastric cancer and colorectal cancer;

3. one or two epitopes in CEA, colon-specific antigen (CSAp) and mucin-1 (MUC-1), with one to three copies of each of the three different specific binding domains, for the treatment of colorectal cancer;

4. one or two epitopes in melanocyte differentiation markers melan-A and/or MITF and/or to one or two epitopes in neuronal markers nestin and/or β3-tubulin, for example, combined with binding domains for binding sites on epithelial markers epithelial membrane antigen and/or epithelial-specific antigen, for the treatment of breast cancer and breast cancer related metastasis;

5. two or more epitopes in carcinoembryonic antigen, for the treatment of lung cancer or bowel cancers;

6. two or more epitopes in CA-125, for the treatment of ovarian cancer;

7. one or more different epitopes, preferably three to five different epitopes in the Her-2/neu receptor, for the treatment of breast cancer, by, for example, preventing tumor outgrowth;

8. one or more epitopes in CD20 combined with binding domains binding to one or more epitopes in CD22, for the treatment of non-Hodgkin's lymphoma with B-cell tumors expressing CD20 and CD22;

9. two or three epitopes in α-fetoprotein, with two or three copies of each different binding domain, for the treatment of germ cell tumors;

10. two or three epitopes in CD52, with two or three copies of each different binding domain, for the treatment of chronic lymphocytic leukemia;

11. one or more epitopes in tumor necrosis factor-α and to one or more epitopes in interleukin-1, for the treatment of rheumatoid arthritis or Crohn's disease;

12. one or more epitopes in vascular endothelial growth factor and to one or more epitopes in epidermal growth factor receptor, for the treatment of colorectal cancer;

13. one or more epitopes in the epidermal growth factor receptor and to the epidermal growth factor receptor mutant form vIII, for the treatment of the brain neoplasm glioblastoma multiforme;

14. two or more epitopes in CD33, for the treatment of acute myelogenous leukemia;

15. one or more epitopes in neuronal markers nestin and β3-tubulin, for the treatment of glioblastomas;

16. one or two epitopes in any selection of B-lymphoid antigens CD10, CD19, CD22, CD34, CD45, and to one or two epitopes in any selection of T-cell markers CD2, CD4, CD5, CD7, CD56, and/or to one or two epitopes in any selection of myeloid markers CD11b, CD13, CD14, CD15, CD33, for the treatment of B acute lymphoblastic leukemia;

17. one or more epitopes in CD38 and to one or more epitopes in CD138, for the treatment of multiple myeloma;

18. one or two epitopes in two or three of the proteins CD38, CD138, CD20 and CD 117, for the treatment of multiple myeloma;

19. two or three epitopes in CD20, with two or three copies of each of the different specific binding domains, resulting in clustering of CD20 into multimers comprising three or more CD20 monomers on the surface of lymphoma cells, for the treatment of lymphomas by inhibiting cell proliferation;

20. one or two epitopes in two or three antigens, or to two or three binding sites in a single antigen, with one to three copies of each of the different specific binding domains, for which the antigen is, for example, CD19, CD20, CD22, CD25, CD33, interleukin-4 receptor, prostate-specific antigen, Lewis(y) carbohydrate, mesothelin, mucin-1, transferrin receptor, prostate-specific membrane antigen, vascular endothelial growth factor, vascular endothelial growth factor receptors, epcam, CTLA-4, for the treatment of oncological diseases;

21. two or three epitopes in cellular death receptor FAS, with two or three copies of each different binding domain, resulting in clustering of four or more FAS molecules into multimers on the surface of targeted cells, resulting in induction of FAS mediated apoptosis, for the treatment of aberrancies comprising FAS expressing aberrant cells;

22. one or more epitopes in cancer cell marker and tumor stroma cell marker versican and to one or more epitopes in Toll-like receptor-2 (TLR2) and/or to one or more epitopes in Toll-like receptor-4 (TLR4) and/or to one or more epitopes in CD 14, for the inhibition of cancer cell invasion and metastasizing mediated by versican-TLR2 and/or versican-TLR4 and/or versican-CD14 interactions;

23. one or more epitopes in TLR2 and to one or more epitopes in TLR4, resulting in an agonistic effect on TLR2/TLR4 activity, for apoptosis mediated anti-tumor therapy after chemotherapy or radiotherapy;

24. two or more epitopes in TLR7, resulting in an agonistic effect on TLR7 activity, for the treatment of basal cell carcinoma;

25. one or two epitopes in two or three antigens, or two or three binding sites in a single antigen for which the antigen is, for example, selected from in general interferons and/or cytokines and/or interleukins and/or chemokines and/or their receptors, and more specifically, for example, selected from CD2, CD4, α-interferon, α-interferon receptor, tumor necrosis factor-α, tumor necrosis factor-α receptor, γ-interferon, γ-interferon receptor, HLA class II antigen receptor, interleukin-1β, interleukin-1β receptor, interleukin 6, interleukin 6 receptor, interleukin 15, interleukin 15 receptor, IgE, IgE receptor, ICAM-1, for the treatment of inflammatory diseases and/or autoimmune diseases;

26. one or two binding sites in CD20 and/or CD30 and/or CD25, combined with at least two binding domains for a binding site on CD16 and/or on CD64, resulting in cross-linking of CD16 on natural killer cells and subsequently lysis of cells bound to natural killer cells, and/or phagocytosis and cellular cytotoxicity exerted on bound cells by CD64-positive cells, respectively, for the treatment of Hodgkin's lymphoma;

27. one or two binding sites on epidermal growth factor receptor or variants thereof, and to one or two binding sites on insulin-like growth factor receptor, for the treatment of a variety of cancers;

28. one or two binding sites on tumor necrosis factor α and to one or two binding sites on CD20, resulting in complement and/or cell mediated lysis when bound to cells, and/or to one or two binding sites on CD80 and/or on CD86, thereby acting as cytotoxic T-lymphocyte associated antigen-4 antagonist, thereby preventing a positive T-cell signal, for the treatment of rheumatoid arthritis;

29. one or more binding sites on human B-cell protein CD19 and/or on CD20 and/or on one or more alternative human B-cell markers, and to epitopes of cytotoxic triggering receptors such as T-cell receptors complexed with CD3 on T-cells and/or FcγRIIIa (CD16) on natural killer cells and/or FCγRI (CD64) and FCAR (CD89) on granulocytes, monocytes and macrophages, for the treatment of non-Hodgkin's lymphoma;

30. one or more binding sites on Her2 and to one or more binding sites on Her1, for the treatment of any aberrancy involving Her2/Her1 expressing aberrant cells, such as, for example, breast cancer;

31. one or more binding sites on MHC 1 α-chain domain α1 and/or domain α2 and/or domain α3 and/or β2 microglobulin, and binding to an MHC 1-peptide complex, for the treatment of tumors presenting the peptides in the context of MHC 1 in a tumor-specific manner;

32. one or more binding sites on MHC 2 α-chain domain α1 and/or domain α2 and/or β-chain domain β1 and/or domain β2, and binding to an MHC 2-peptide complex, for the treatment of tumors presenting the peptides in the context of MHC 2 in a tumor-specific manner;

33. one or more binding sites on MART-1 and/or on gp100 and/or on tyrosinase, for the treatment of melanomas;

34. one or more binding sites in any single molecule or in any combination of two or more molecules selected from the following prostate cancer related antigens, prostate-specific antigen (PSA, also referred to as kallikrein 3 (KLK3)), Thomsen-Friedenreich (TF) antigen, prostate stem cell antigen, prostatic acid phosphatase (PAP, also prostatic-specific acid phosphatase (PSAP)), human HLA-A2 restricted CD8+ T-cell epitopes, e.g., nonamer peptides FLFLLFFWL (SEQ ID NO:13) (from prostatic acid phosphatase), (SEQ ID NO:14) TLMSAMTNL (from prostatic acid phosphatase), ALDVYNGLL (SEQ ID NO:15) (from prostatic acid phosphatase), human HLA-A2.1-restricted CTL epitope ILLWQPIPV (SEQ ID NO:16) (from prostatic acid phosphatase-3), six-transmembrane epithelial antigen of prostate (STEAP), human HLA-A2.1-restricted CTL epitope LLLGTIHAL (SEQ ID NO:17) (from STEAP-3), mucins (MUC-1 and -2), MUC-1-32mer (CHGVTSAPDTRPAPG-STAPPAHGV TSAPDTRPA) (SEQ ID NO:18), Globo H, Lewis<sup>y</sup>, Tn(c), TF(c) clusters, GM2, prostate-specific membrane antigen (PSMA), kallikrein 4, prostein, HLA-A2.1-restricted epitopes from BA46, PTH-rP, HER-2/neu, hTERT, and MAGE-A8. for the treatment of prostate cancer 35. two or more of the T-cell epitopes selected from 146-KLQCVDLHV-154 (SEQ ID NO:19), 141-FLTPKKLQCV-150 (SEQ ID NO:20), 154-VISNDV-CAQV-163 (SEQ ID NO:21), 154-YISNDVCAQV-163 (SEQ ID NO:22) of PSA, presented by HLA-A2 and/or 162-QVHPQKVTK-170 (SEQ ID NO:23) of PSA, presented by HLA-A3, and/or 152-CYASGWGSI-160 (SEQ ID NO:24), 248-HYRKWIKDTI-257 (SEQ ID NO:25) of PSA, presented by HLA-A24, and/or 4-LLHETDSAV-12 (SEQ ID NO:26), 711-ALFDIESKV-719 (SEQ ID NO:27), 27-VLAGGFFLL-35 (SEQ ID NO:28) of PSMA, presented by HLA-A2, and/or 178-NYARTEDFF-186 (SEQ ID NO:29), 227-LYSDPADYF-235 (SEQ ID NO:30), 624-TYSVSFDSL-632 (SEQ ID NO:31) of PSMA, presented by HLA-A24, and/or 299-ALDVYNGLL-307 (SEQ ID NO:32) of PAP, presented by HLA-A2 and/or 213-LY-CESVHNF-221 (SEQ ID NO:33) of PAP, presented by HLA-A24 and/or 199-GQDLFGIWSKVYDPL-213 (SEQ ID NO:34), 228-TEDTMTKLRELSELS-242 (SEQ ID NO:35) of PAP, presented by MHC-2 and/or 14-ALQPGTALL-22 (SEQ ID NO:36), 105-AILALLPAL-113 (SEQ ID NO:37), 7-ALLMAGLAL-15 (SEQ ID NO:38), 21-LLCYSCKAQV-30 (SEQ ID NO:39) of PSCA, presented by HLA-A2 and/or 155-LLANGRM-PTVLQCVN-169 (SEQ ID NO:40) of Kallikrein 4, presented by DRB1*0404 and/or 160-RM-PTVLQCVNVSVVS-174 (SEQ ID NO:41) of Kallikrein 4, presented by DRB1*0701 and/or 125-SVSESDTIRSISIAS-139 (SEQ ID NO:42) of Kallikerein 4, presented by DPB1*0401, preferably combined with binding domains binding to the indicated MHC molecule exposing the listed T-cell epitopes, for the treatment of prostate cancer;

36. one or two epitopes in each protein in any combination of two or three of the proteins NY-ESO-1, Her2/neu, Mesothelin, cancer antigen (CA) 15-3, carcinoembryonic antigen and CA-125, with one or two copies of each different binding domain, for the treatment of ovarian cancer;

37. one epitope in each of the six proteins NY-ESO-1, Her2/neu, Mesothelin, cancer antigen (CA) 15-3, carcinoembryonic antigen and CA-125, for the treatment of ovarian cancer;

38. a binding site in the T-cell epitope peptide 369-376 from human Her-2/neu and/or to a binding site in the MHC-peptide 369-376 complex, and to one or more binding sites in surface expressed Her-2/neu and/or to one or more binding sites in surface expressed Her-1, for the treatment of malignancies related to Her-2 and/or Her-1 over-expression.

39. One or two epitopes of the CD44 splice variants known as CD44, -v6, CD44-v9, CD44-v10 and/or to one or two epitopes in CD38 and in CD138, for the treatment of multiple myeloma;

40. one or two epitopes of Epcam and/or to one or two epitopes in the folate receptor, for the treatment of various cancers and for the treatment of ovarian cancer, specifically;

41. one or two epitopes of CAIX and/or to one or two epitopes in CD70, for the treatment of renal cancer;

42. one or more epitopes in PDGF receptor and to one or more epitopes in VEGF receptor, for the treatment of various cancers accompanied by co-expression of the two receptors on the surface of tumor cells;

43. one or more epitopes in ErbB1 and to one or more epitopes in ErbB2, with one and more preferably two or three binding domains for each binding site, for the treatment of various cancers accompanied by co-expression of the two surface molecules on tumor cells.

Of particular interest are of course combinations of surface molecules expressed by aberrant cells, with each individual surface molecule bearing features unique to the aberrant cell. As said, these targets are however rare. Table 1 gives a list of tumors on which targets have been found that are unique to the aberrant cells. These unique targets are T-cell epitopes derived from various Cancer Testis antigens like, but not limited to MAGE variants complexed with MHC molecules. It is easy using a binding domain according to the disclosure to identify tumors that present the target MHC-peptide complexes. This can be done in vitro or in vivo (imaging). Thus, high specificity for aberrant cells is achieved when binding domains are combined in proteinaceous molecules of the disclosure that target binding sites in two or more surface molecules unique to the aberrant cell. Such molecules of the disclosure provide even an higher specificity than molecules of the disclosure targeting two different antigens which are co-expressed on aberrant cells, with one of the two, or both antigens also (moderately) expressed on healthy cells. An example is the co-expression on melanoma cells of two T-cell receptor epitopes unique to the aberrant cell, i.e., the MAGE-A peptide YLEYRQVPG (SEQ ID NO:43) presented by MHC 1 HLA-A0201 and the MAGE-A peptide EGDCAPEEK (SEQ ID NO:44) presented by MHC-1 HLA-CW7. Targeting these two melanoma cell-specific binding sites by proteinaceous molecules of the disclosure provides highly specific binding. When only one such tumor-specific MHC-peptide complex is present on aberrant cells, efficacious proteinaceous molecules of the disclosure comprise, for example, two or three different binding domains specific for that complex, and binding domains binding to the specific type of MHC 1 HLA-molecule.

Alternatively or additively, binding domains binding to the MHC-peptide complex are linked to binding domains binding to cell-surface proteins specifically expressed by the melanocyte lineage, such as MART-1, gp100 and tyrosinase. Combining binding domains with high affinity for tumor cell-specific antigens (i.e., MHC-MAGE peptide complex) with binding domains with low affinity for surface markers of the melanocyte lineage further improves the specificity of the proteinaceous molecules of the disclosure for the aberrant cells. Especially when the affinity for the surface markers of the melanocyte lineage is below a certain threshold prohibitive for binding of the proteinaceous molecules of the disclosure to healthy cells in the melanocyte lineage.

Other examples of proteinaceous molecules of the disclosure comprising at least two different specific binding domains that target binding sites on surface molecules expressed by aberrant cells and not/hardly by healthy cells are proteinaceous molecules binding to A33 and to fibroblast activation protein, for the treatment of colorectal cancer. Yet another example of two different target binding sites on tumor cells, suitable for targeting by multi-specific proteinaceous molecules of the disclosure are Das-1 and CEA. Binding molecules targeting both Das-1 and CEA are, for example, suitable for the treatment of esophageal cancer.

For some tumors, only one tumor marker on the surface of the aberrant cells has been identified so far. As an example for these occasions, the proteinaceous molecules of the disclosure comprise different binding domains binding to at least one binding site on a tumor marker and binding to at least one binding site on a cell-surface molecule specific for the tissue associated with the tumor.

A good source for selecting binding sites suitable for specific targeting of aberrant cells by proteinaceous molecules of the disclosure, is the Peptide Database listing T-cell defined tumor antigens (Van den Eynde et al., Curr. Opin. Immunol. 1997; Houghton et al., Curr. Opin. Immunol. 2001; van der Bruggen et al., Immunol. Rev. 2002; Parmiani et al., J. Immunol. 2007; On the World Wide Web at cancerimmunity.org/peptidedatabase/Tcellepitopes.htm).
The database provides combinations of antigen peptides complexed with MHC molecules comprising the indicated class of HLA, unique to tumor cells or over-expressed by tumor cells.

Example 2

Selection of Antibody Fragments

Multi-specific proteins are built from any antigen binding domain, such as, but not limited to, antibodies, alpha-helices and T-cell receptors. Antibody Vh fragments specific for tumor associated surface antigens and MHC-restricted antigens are derived from hybridoma cells producing mouse, rat, rabbit, llama or human antibodies. Antibody fragments can also be obtained after immunization of animals with (partly) purified antigen, tumor cells or tumor cell lysate. Alternatively, antibody fragments of human, mouse, rat or llama origin can be obtained from antibody phage, yeast, lymphocyte or ribosome display libraries. Such antibody libraries (scFv, Fab, Vh or Vhh) may be constructed from non-immunized species as well as immunized species.

2.1: Selection of Human Antibody Fragments Specific for MHC-Restricted Cancer Testis Antigens To obtain human antibody fragments specific for, e.g., MHC presented epitopes, a Human antibody Fab, VHCH or Vh phage display library will be used for selections essentially as described by Chames et al., Human Fab phages ($10^{13}$ colony forming units) are first pre-incubated for one hour at room temperature in PBS containing 2% non-fat dry milk (PBSM). In parallel, 200 μl Streptavidin-coated beads (Dynal) are equilibrated for one hour in PBSM. For subsequent rounds, 100 μl beads are used. To deplete for pan-MHC binders, to each selection round, 200 nM of biotinylated MHC class I-peptide (MHC-p) complexes containing an irrelevant peptide (Sanquin, the Netherlands) are added to the phages and incubated for 30 minutes under rotation. Equilibrated beads are added, and the mixture is incubated for 15 minutes under rotation. Beads are drawn to the side of the tube using magnetic force. To the depleted phage fraction, subsequently decreasing amounts of biotinylated MHC-p complexes (200 nM for the first round, and 20 nM for the second and third round) are added and incubated for one hour at room temperature, with continuous rotation. Simultaneously, a pan-MHC class I binding soluble Fab (D3) is added to the phage-MHC-p complex mixture (50, 10, and 5 μg for rounds 1-3, respectively). Equilibrated streptavidin-coated beads are added, and the mixture incubated for 15 minutes under rotation. Phages are selected by magnetic force. Non-bound phages will be removed by five washing steps with PBSM, five steps with PBS containing 0.1% Tween, and five steps with PBS. Phages are eluted from the beads by ten minutes incubation with 500 μl freshly prepared tri-ethylamine (100 mM). The pH of the solution is then neutralized by the addition of 500 μl 1 M Tris (pH 7.5). The eluted phages are incubated with logarithmic growing E. Coli TG1 cells ($OD_{600nm}$ of 0.5) for 30 minutes at 37° C. Bacteria are grown overnight on 2×TYAG plates. Next day, colonies are harvested, and a 10 μl inoculum is used in 50 ml 2×TYAG. Cells are grown until an $OD_{600nm}$ of 0.5, and 5 ml of this suspension is infected with M13k07 helper phage ($5\times10^{11}$ colony forming units). After 30 minutes incubation at 37° C., the cells are centrifuged, resuspended in 25 ml 2×TYAK, and grown overnight at 30° C. Phages are collected from the culture supernatant as described previously, and used for the next round panning. After two, three or four selection rounds enrichment of specific binders is obtained, and individual clones are analyzed for binding to specific peptide/MHC complexes by ELISA.

2.2: Human Fab Specific for the MHC Presented Peptide Epitopes Bind Antigen Positive Cells Selected Fab phages are then analyzed for their capacity to bind MHC-positive EBV-transformed B-LCL loaded with the peptide epitopes. For HLA-A0201 presented epitopes the B-LCL line BSM ($0.5\times10^6$) is loaded with peptide epitopes (10 μg in 100 μl PBS) for 30 minutes at 37° C., followed by incubation with the Fab phages and analyzed by flow-cytometry.

Phages are then used to stain tumor cell lines of distinct histologic origin and analyzed by flow cytometry.

Example 3

Production of Multi-Specific Proteins Comprising Camelized Single Domain Vh Domains 3.1: Design of Genes for Production of Multi-Specific Vh Proteins Human antibody germline gene VH3 demonstrates high homology to llama single domains VHH. Exchange of amino acids 44, 45 and 47 in the human VH3 genes by amino acids present in llama VHH at these positions has shown to enhance stability and expression of the human VH3 genes (Riechmann, Muyldermans, 199). For expression and stability many of the selected human Vh might benefit from the exchange of amino acids 44, 45 and 47 by llama VHH amino acids, a process called camelization. A gene comprising at least two distinct human Vh domains binding to at least two distinct MHC/peptide epitopes will be compiled such that upon expression it would comprise six Vh domains. To this end a gene will be designed comprising the pelB secretion signal, which will be operatively linked to six codon-optimized, camelized Vh domains with linkers (($Gly_4Ser)_n$ (SEQ ID NO:45), $(GSTSGS)_n$ (SEQ ID NO:46), GSTSGSGKPGSGEGSTKG (SEQ ID NO:47), EFAKT-TAPSVYPLAPVLESSGSG (SEQ ID NO:48) or any other linker that provides flexibility for protein folding, or, EPKSCDKTHT (SEQ ID NO:49) (IgG1), ELKTPLGDTTHT (SEQ ID NO:50) (IgG3), or ESKYGPP (SEQ ID NO:51) (IgG4)) between each Vh domain. This gene will, for example, be synthesized by Geneart (Regensburg, Germany) and cloned into the pStaby 1.2 vector (Delphi genetics, Belgium) for expression in E. coli.

Example 4

Production and Purification of Hexameric AH5 Vh Protein

For expression of multi-specific Vh proteins the pStaby-multispecific-protein vectors will be introduced via electroporation into SE1 bacteria. Positive clones will be grown in the presence of 2% glucose at 25° C. to 30° C. until $OD_{600}$=0.8. Bacterial TYAG medium will then be replaced with TY medium containing 0.1-1 mM IPTG to induce expression. After overnight culture at 25° C. to 30° C., bacteria and medium will be harvested. The periplasm fraction will be collected after incubation of bacteria with PBS/EDTA/NaCl for 30 minutes on ice. Protein expression will then be analyzed by SDS-PAGE.

Multi-specific Vh proteins will be isolated from media and bacteria using Ni-affinity purification. To this end medium will be incubated with Ni-coupled Sepharose-beads and incubated overnight while stirring gently. To obtain intracellular proteins bacteria will be lysed and cellular debris removed by centrifugation. After overnight dialysis with PBS multi-specific Vh proteins will be purified with Ni-Sepharose. Purity of the multi-specific Vh proteins will be analyzed by SDS-PAGE and protein concentration determined by BCA protein assay (Pierce).

Example 5

Construction of Multi-Specific Genes to Improve Circulation and Tumor Penetration The pharmacokinetic properties of therapeutic proteins, e.g., their distribution, metabolism and excretion are dependent on factors such as shape, charge and size. Most small plasma molecules (MW<50-60 kDa) possess very short half-life, whereas larger plasma proteins such as human serum albumin (HSA) and immunoglobulins (Ig) have very long half-lives (19 days for HSA, one to four weeks for Ig). Indeed, addition of IgG-Fc or Human serum albumin has shown to extend circulation time, tumor penetration and antitumor effects when linked to therapeutic proteins. In addition the coupling of IgG-Fc to the multi-specific proteins will allow recruitment of immune cells to the tumor site allowing immune-specific responses against the cancerous tissue.

5.1: Construction of Multi-Specific Proteins with IgG1-Fc and Human Serum Albumin The multi-specific construct will be linked to the IgG1-Fc region or to human serum albumin, codon optimized for expression in eukaryotic cells and cloned into the pcDNA-3.1+ vector (Geneart, Regensburg, Germany).

Example 6

Isolation and Cloning of a MAGE-1 Specific (scFv)-TCR from the CD8+ CTL Clone 82/30

Standard cloning techniques were used in the examples below. Techniques are described in: Molecular Cloning; A Laboratory Manual (Cold Spring Harbor Press, Cold Spring Harbor, N.Y.) by Maniatis, T. et al. or in cited publications.

Cloning of the TCR Vβ

The TCR is a heterodimer which consists of an α and a β chain. The TCR α and β chains are members of the immunoglobulin gene superfamily and are generated by combined associations of V, J, D and C genes. The TCR polypeptides are disulfide linked, highly polymorphic in their N-terminal, variable domains and responsible for antigen recognition. Obtaining the TCR from the MAGE-1 specific CTL clone 82/30 (Traversari, C. et al., 1992) was achieved by polymerase chain reaction (PCR; Maniatis, T. et al.) amplification of cDNA obtained from this CTL clone.

To obtain cDNA, total RNA was isolated from T cell clone 82/30 cells according to the method by Chomczynski et al. (Chomczynski, P. and Sacchi, N., 1987) and transferred into cDNA essentially as described by Maniatis et al. Amplification of cDNA sequences by PCR is possible only if the sequence of the gene of interest is known. In general, for PCR, two primers complementary to the 5' end and the 3' end of the sequence are used as the initiation point of DNA synthesis. Because the sequence of the 5' ends of the TCR α and β chain from T cell clone 82/30 were unknown, a PCR method, referred to as RACE (rapid amplification of cDNA ends) was used to amplify the TCR α chain. The TCR β chain was amplified by RACE-PCR using primers described in Table 2.

Oligonucleotide primers used to synthesize the α and β chain cDNA and amplify the Vα, Vβ and Cβ gene segments (Table 2)

A fragment of about 350-450 base pairs was isolated from the agarose gel, purified and ligated into pBluescript (Stratagene, USA). The ligation mixture was introduced into bacteria which were selected and expanded. DNA was isolated from these selected bacterial colonies and analyzed by restriction enzyme digestion to confirm the presence of the amplified TCR β fragment.

Three positive colonies were subjected to DNA sequencing. The sequences of these three individual clones were compared and found to be identical. The sequence obtained from the amplified TCR β fragments however did not include the signal sequence of the TCR β gene. To obtain the complete sequence of the TCR-V β gene, this partial sequence was compared with all known TCR β sequences. Alignment of the sequences showed almost 100% homology to sequences from the TCR β family 1 (TCRβ.1). Based on this sequence homology, a primer was synthesized complementary to the 5' end of the TCR β.1 and used to amplify the complete TCR variable β.1 domain. The DNA was subjected to "direct sequencing," Analysis of the obtained sequence showed 100% homology of the amplified TCR β fragment to the signal sequence and major part of the variable region of the TCR β chains from the TCR β family 1. Based on this sequence primers were designed that allowed cloning of the TCR variable β chains in a single chain TCR construct.

Example 7

Cloning of the TCR α Chain

For cloning of the TCR α chain, a different approach was followed. First, to determine to which family the TCR Vα chain belongs, a family typing PCR was performed. Twenty-one different TCR variable α chains have been described. In a family typing PCR, the template cDNA was divided into separate samples that are each individually amplified with a family specific 5' primer and a constant primer. Multiple PCR reactions had yielded amplified fragments. In order to determine which fragment corresponded to the TCR Vα fragment, a Southern blot was performed with a $^{32}$P-labelled Cα probe. A positive signal was observed only in the PCR reaction which was performed with the TCR α primer corresponding to family number 12. The remaining of the DNA of this PCR reaction was purified with primer removal as described above and subjected to DNA sequencing. The obtained sequence was compared to the TCR α sequence of the only known member of family number 12. Except for the diversity region, 100% homology was observed. This allowed the design of primers which could be used for the amplification of the complete variable region of the TCR α chain. The sequences of Vα and Vβ of the TCR derived from CTL clone 82/30 are given as SEQ ID. NO:1 and SEQ ID. NO:2, respectively.

Example 8

8.1 Construction of Two Domain Single Chain TCR Molecules.

For construction of single chain TCR molecules, a cloning vector was designed that allows easy construction of single chain molecules. The vector was made by replacement of the multiple cloning sites in pBluescript (Stratagene) by a specially designed polylinker (Table 3). For cloning of the TCR Vα and TCR Vβ fragments, primers were designed that allowed cloning of these fragments in front of the flexible linker sequence or after the linker sequences.

For amplification of the TCR Vα and TCR Vβ fragments, two separate PCR reactions were performed to generate fragments that include the signal sequence of the V region and fragments that start practically at the beginning of the mature protein. The DNA fragments were digested with restriction enzymes that allow cloning next to the flexible linker. Positive bacterial colonies were grown for DNA purification and DNA was subjected to DNA sequencing. DNA clones with the correct sequence were used to construct the chimeric single chain TCR constructs. The clones containing either the TCR Vα or the TCR Vβ fragments in front of the flexible linker sequence were then ligated to the TCR Vα and TCR Vβ fragments which lack the signal sequence. In this way, three different single chain TCRs were constructed (Vα-212 linker-Vβ, Vβ-212 linker-Vα and Vα-(Gly$_4$Ser)$_3$, linker-Vβ).

8.2 Construction of the Bispecific Anti-CD3×scTCR ßαMolecule.

The scTCR ßα was cloned next to the anti-CD3 specific scFv obtained from OKT-3 cells and introduced into the pBullet retroviral vector. A schematic presentation of the scFv×scTCR is given in FIG. 3.

Example 9

The pBullet retroviral vector was introduced into HEK 293T cells by calcium-phosphate transfection. Supernatant from these cells was harvested 4 days after transfection and used for diverse experiments.

9.1 The scFv×scTCR Binds Primary Human T Lymphocytes.

Primary human T lymphocytes were isolated from blood by standard fycol separation and incubated with the supernatant of transfected HEK 293T cells. After an incubation period of 30 minutes on ice, the cells were washed and incubated with a Fluorescein isothiocyanate (FITC)-labelled TCR Vα-12.1 specific monoclonal antibody (mAb) or an irrelevant FITC-labelled mAb. After an incubation period of 30 minutes on ice cells were washed, fixed with phosphate-buffered saline (PBS) 1% paraformaldehyde (PFA) and analysed by flow-cytometry. As shown in FIG. 4, the bispecific scFv×scTCR binds to the primary human T-lymphocytes.

Example 10

Primary human T-lymphocytes labelled with the bispecific scFv anti-CD3×scTCR ßα specifically kill HLA-A01/MAGE-A1 positive melanoma cells.

Primary human T-lymphocytes, activated for two days with immobilised OKT-3 were labelled with the scFv×scTCR and incubated with 51Cr-labelled HLA-A 1, MAGE-A1 positive melanoma cells (MZ2-MEL 3.0) and HLA-A1 positive, MAGE-A1 negative melanoma cells (MZ-MEL 2.2.). 51Cr-release was measured after an incubation period of 4 hours and showed that only HLA-A1/MAGE-A1 MZ2-MEL 3.0 melanoma cells were killed by the scFv×scTCR labelled T-lymphocytes (FIG. 5).

Example 11

11.1 Construction of a Bispecific Single Domain (sd) Ab VH×VH with Specificity for the HLA-A0201 Presented Multi-MAGE-a Peptide and Human CD3.

A gene was composed from the camelized human AH5 VH and camelized mouse anti-CD3 VH (obtained from OKT-3). The resulting sequence of the sdAb AH5×CD3 was compiled by gene synthesis by GeneArt (Regensburg, Germany), and cloned into the pStaby 1.2 expression vector. See SEQ ID NO:3 for the DNA sequence of this bispecific single domain antibody (BsdAB) AH5×CD3, and SEQ ID NO:4 for the amino-acid sequence of BsdAB AH5×CD3.

TABLES

TABLE 1

Examples for the frequency of MAGE-A expression by human cancers.
Frequency of expression (%)

| Cancer | MAGE-A1 | MAGE-A2 | MAGE-A3 | MAGE-A4 | MAGE-A6 | MAGE-A10 | MAGE-A11 |
|---|---|---|---|---|---|---|---|
| Melanoma | 16 | E | 36 | E | 64 | E | 74 |
| Head and neck | 25 | 42 | 33 | 8 | N | N | N |
| Bladder | 21 | 30 | 35 | 33 | 15 | N | 9 |
| Breast | 6 | 19 | 10 | 13 | 5 | N | N |
| Colorectal | N | 5 | 5 | N | 5 | N | N |
| Lung | 21 | 30 | 46 | 11 | 8 | N | N |
| Gastric | 30 | 22 | 57 | N | N | N | N |
| Ovarian | 55 | 32 | 20 | E | 20 | N | N |
| Osteosarcoma | 62 | 75 | 62 | 12 | 62 | N | N |
| Hepatocarcinoma | 68 | 30 | 68 | N | 30 | 30 | 30 |
| Renal cell carcinoma | 22 | 16 | 76 | 30 | N | N | N |

E, expressed but the frequency is not known;

N, expression by tumors has never been observed

TABLE 2

| Oligonucleotide Primers | |
|---|---|
| Vα-ATG: | 5' GCG AAT TCT ACG TAC CAT GAA CAT GCT GAC TGC CAG C3' (SEQ ID NO: 5) |
| Vα-3': | 5' CGT CTA GAG GAC AGA AGG TAA CTC AAG CGC AG 3' (SEQ ID NO: 6) |

TABLE 2-continued

| Oligonucleotide Primers | |
|---|---|
| Vβ-ATG: | 5' CCG AAT TCT ACG TAC CAT GGG CTT CAG GCT GCT CTG 3' (SEQ ID NO: 7) |
| Vβ-3': | 5' GCG GAT CCG AGC ACT GTC AGC CGG GTG CC 3' (SEQ ID NO: 8) |

TABLE 3

212 LINKER

5' GTA CGA ATT CGC AGA TCT GGC TCT ACT TCC GGT AGC AAATCC
TCT GAA GGC AAA GGT ACT AGT GCG GAT CCG GCT CGA GCA GCT 3'
(SEQ ID NO: 9)

(GLY)₄SER₃ LINKER

5' GAT CCG GTG GAG GCG GTT CAG GCG GAG GTG GCT CTG GCG
GTG GCG GAT CGA 3' (SEQ ID NO: 10)

SEQ ID NOs

SEQ ID. NO: 1: DNA sequences of the HLA-A1/MAGE-A1 specific TCR variable
region Valpha obtained from CTL 82/30
ATG AAC ATG CTG ACT GCC AGC CTG TTG AGG GCA GTC ATA GCC
TCC ATC TGT GTT GTA TCC AGC ATG GCT CAG AAG GTA ACT CAA GCG CAG ACT
GAA ATT TCT GTG GTG GAG AAG GAT GTG ACC TTG GAC TGT GTG TAT GAA
ACC CGT GAT ACT ACT TAT TAC TTA TTC TGG TAC AAG CAA CCA CCA AGT GGA
GAA TTG GTT TTC CTT ATT CGT CGG AAC TCT TTT GAT GAG CAA AAT GAA ATA
AGT GGT CGG TAT TCT TGG AAC TTC CAG AAA TCC ACC AGT TCC TTC AAC TTC
ACC ATC ACA GCC TCA CAA GTC GTG GAC TCA GCA GTA TAC TTC TGT GCT CTG
GGA GGG GTG AAT AAT AAT GCA GGC AAC ATG CTC ACC TTT GGA GGG GGA ACA
AGG TTA ATG GTC AAA CCC (SEQ ID. NO: 1)

SEQ ID NO: 2: DNA sequences of the HLA-A1/MAGE-A1 specific TCR variable
region Vbeta obtained from CTL 82/30
ATG GGC TTC AGG CTG CTC TGC TGT GTG GCC TTT TGT CTC CTG
GGA GCA GGC CCA GTG GAT TCT GGA GTC ACA CAA ACC CCA AAG CAC CTG ATC
ACA GCA ACT GGA CAG CGA GTG ACG CTG AGATGC TCC CCT AGG TCT GGA GAC
CTC TCT GTG TAC TGG TAC CAA CAG AGC CTG GAC CAG GGC CTC AGT TCC TC
ATT CAC TAT TAT AAT GGA GAA GAG AGA GCA AAA GGA AAC ATT CTT GAA CGA
TTC TCC GCA CAA CAG TTC CCT GAC TTG CAC TCT GAA CTA AAC CTG AGC TCT
CTG GAG CTG GGG GAC TCA GCT TTG TAT TTC TGT GCC AGC AAC ATA GCG GGC
GGG AGT TAT ACG CAG TAT TTT GGC CCA GGC ACC CGG CTG ACA GTG CTC (SEQ
ID. NO: 2)

SEQ ID. NO: 3: DNA sequence of bispecific single domain antibody (BsdAB)
AH5 x CD3
ATGAAATACCTATTGCCTACGGCAGCCGCTGGATTGTTATTACTCGCG
GCCCAGCCGGCCATGGCCCAGCTGCAGCTGCAGGAGTCCGGGGGAGGCGTGGTCCAG
CCTGGGAGGTCCCTGAGACTCTCCTGTGCAGCCTCTGGATTCACCTTCAGTAGCTATG
GCATGCACTGGGTCCGCCAGGCTCCAGGCAAGGAGAGAGAGGGGGTGGCAGTTATAT
CATATGATGGAGTAATAAATACTATGCAGACTCCGTGAAGGGCCGATTCACCATCTC
CAGAGACAATTCCAAGAACACGCTGTATCTGCAAATGAACAGCCTGAGAGCTGAGGA
CACGGCTGTGTATTACTGTGCCGGTGGGAGCTACTACGTCCCGGACTACTGGGGCCAG
GGAACCCTGGTCACCGTCTCAAGCGCGGCCGCAGGTGGCGGAGGGTCTGGTGGCGGA
GGGTCTGGTGGCGGAGGGTCGCAGGTGCAGCTGCAGCAGTCTGGGGCTGAACTGGCA
AGACCTGGGGCCTCAGTGAAGATGTCCTGCAAGGCTTCTGGCTACACCTTTACTAGGT
ACACGATGCACTGGGTAAAACAGAGGCCTGGACAGGGTCTGGAATGGATTGGATACA
TTAATCCTAGCCGTGGTTATACTAATTACAATCAGAAGTTCAAGGACAAGGCCACATT
GACTACAGACAAATCCTCCAGCACAGCCTACATGCAACTGAGCAGCCTGACATCTGA
GGACTCTGCAGTCTATTACTGTGCAAGATATTATGATGATCATTACTGCCTTGACTACT
GGGGCCAAGGCACCACTCTCACAGTCTCCTCAGGGGCCGCAGAACAAAAACTCATCT
CAGAAGAGGATCTGAATGGGCCCATCATCATCATCATCACTAA (SEQ ID. NO:3)

SEQ ID NO: 4: Amino acid sequence of bispecific single domain antibody
(BsdAB) AH5 x CD
MKYLLPTAAAGLLLLAAQPAMAQLQLQESGGGVVQPGRSLRLSCAASG
FTFSSYGMHWVRQAPGKEREGVAVISYDGSNKYYADSVKGRFTISRDNSKNTLYLQMNS
LRAEDTAVYYCAGGSYYVPDYWGQGTLVTVSSAAAGGGGSGGGGSGGGGSQVQLQQS
GAELARPGASVKMSCKASGYTFTRYTMHWVKQRPGQGLEWIGYINPSRGYTNYNQKFK
DKATLTTDKSSSTAYMQLSSLTSEDSAVYYCARYYDDHYCLDYWGQGTTLTVSSGAAEQ
KLISEEDLNGAHHHHHH (SEQ ID NO: 4)

REFERENCES

Ridgway J. B., L. G. Presta, and P. Carter. "Knobs-into-holes" engineering of antibody CH3 domains for heavy chain heterodimerization. *Protein Engineering* 1996, 9(7):617-621.

Van den Eynde B. J., and P. van der Bruggen. T cell-defined tumor antigens. *Curr. Opin. Immunol.* 1997, 9:684-93.

Houghton A. N., J. S. Gold, and N. E. Blachere. Immunity against cancer: lessons learned from melanoma. *Curr. Opin. Immunol.* 2001, 13:134-40.

van der Bruggen P., Y. Zhang, P. Chaux, V. Stroobant, C. Panichelli, E. S. Schultz, J. Chapiro, B. J. Van den Eynde, F. Brasseur, and T. Boon. Tumor-specific shared antigenic peptides recognized by human T cells. *Immunol. Rev.* 2002, 188:51-64.

Parmiani G., A. De Filippo, L. Novellino, and C. Castelli. Unique human tumor antigens: immunobiology and use in clinical trials. *J. Immunol.* 2007, 178:1975-9.

Chames P., H. R. Hoogenboom, and P. Henderikx. Selection of antigens against biotinylated antigens. In Antibody phage display, methods and protocols, edited by P. M. O'Brien and R. Aitken. *Methods in Molecular Biology* 2002, 178:147-159.

Lutz Riechmann and Serge Muyldermans. Single domain antibodies: comparison of camel VH and camelized human VH domains. *Journal of Immunological Methods* 1999, 231:25-38.

Maniatis T., et al. Molecular Cloning; A Laboratory Manual (Cold Spring Harbor Press, Cold Spring Harbor, N.Y.) 1989.

Traversari, C. et al., *J. Exp. Med* 1992, 176:1453-1457.

Chomczynski, P. and Sacchi, N., *Anal. Biochem* 1987. 162: 156-159.

---

The invention claimed is:

1. A polypeptide comprising SEQ ID NO:4.

2. A single polypeptide chain that targets T cells to a cell expressing MAGE-A, the single polypeptide chain comprising:
   at least one T cell receptor ("TCR") Vα and Vβ domain that binds to an MAGE-A HLA epitope; and
   a single polypeptide chain antibody ("scFv") that binds human CD3; and
   wherein the MAGE-A HLA epitope consisting of the MAGE-A peptide SEQ ID NO:43 presented by MHC class I HLA-A0201 and/or the MAGE-A peptide SEQ ID NO:44 presented by MHC class I HLA-CW7.

3. The single polypeptide chain of claim 2, wherein the single polypeptide chain comprises:
   a fusion protein comprising a single chain antibody from OKT3 (VH-VL) that binds to human CD3, fused to a linker,
   a human single chain T cell receptor ("TCR") Vβ-1 encoded by SEQ ID NO: 2, a second linker, and TCR Vα-12 encoded by SEQ ID NO: 1.

4. An isolated polypeptide chain comprising SEQ ID NO: 4.

5. A bispecific single domain antibody comprising:
   a first variable domain ("Vh") that binds to MAGE-A peptide SEQ ID NO: 43 presented by MHC class I HLA-A0201, and
   a second Vh that binds to human CD3,
      wherein the antibody comprises the amino acid sequence of SEQ ID NO: 4.

6. The bispecific single domain antibody of claim 5, wherein at least one of the first and second Vh is a camelized human Vh domain.

7. A single polypeptide chain that targets T cells to a cell expressing MAGE-A, the single polypeptide chain comprising:
   a human T cell receptor ("TCR") Vα-12.1 and Vβ-1 domain that binds to an MAGE-A HLA epitope, and
   a single chain antibody ("scFv") that binds human CD3,
   wherein the MAGE-A HLA epitope consisting of MAGE-A peptide SEQ ID NO: 43 presented by MHC class I HLA-A0201 or MAGE-A peptide SEQ ID NO: 44 presented by MHC class I HLA-CW7, and
   wherein the TCR Vβ-1 domain is encoded by SEQ ID NO: 2 and the TCR Vα-12.1 is encoded by SEQ ID NO: 1.

8. A single polypeptide chain that targets T cells to a cell expressing MAGE-A, the single polypeptide chain comprising:
   a first variable immunoglobulin domain that binds a MAGE-A HLA epitope, wherein the first variable immunoglobulin domain is a variable domain of a heavy chain of an immunoglobulin ("Vh"), and wherein the MAGE-A HLA epitope comprises the MAGE-A peptide SEQ ID NO:43 presented by MHC class I HLA-A0201;
   a second variable immunoglobulin domain, different from the first variable immunoglobulin domain and being a Vh, wherein the second variable immunoglobulin domain binds human CD3; and
   at least one linker linking the first variable immunoglobulin domain and the second variable immunoglobulin domain through peptide bonds, thus separating the first variable immunoglobulin domain and second variable immunoglobulin domain from one another,
   wherein the single polypeptide chain is a bispecific single domain antibody, and
   wherein the single polypeptide chain comprises the amino acid sequence of SEQ ID NO: 4.

9. A single polypeptide chain that targets T cells to a cell expressing MAGE-A, the single polypeptide chain comprising:
   at least one T cell receptor ("TCR") Vα and Vβ domain that binds to an MAGE-A HLA epitope, wherein the (TCR) comprises Vα-12.1 domain and Vβ-1 domain that binds to an MAGE-A HLA epitope; and
   a single polypeptide chain antibody ("scFv") that binds human CD3;
   wherein the MAGE-A HLA epitope consisting of the MAGE-A peptide SEQ ID NO:43 presented by MHC I class HLA-A0201 or the MAGE-A peptide SEQ ID NO:44 presented by MHC-I class HLA-CW7, and
   wherein the TCR Vβ-1 domain is encoded by SEQ ID NO: 2 and the TCR Vα-12.1 is encoded by SEQ ID NO: 1.

10. An antibody that targets T cells to a cell expressing MAGE-A, the antibody comprising:
    at least one T cell receptor ("TCR") Vα domain and Vβ domain that binds to an MAGE-A HLA epitope; and
    a single polypeptide chain antibody ("scFv") that binds human CD3,
    wherein the MAGE-A HLA epitope consisting of:
       the MAGE-A peptide SEQ ID NO:43 presented by MEW class I HLA-A0201, or
       the MAGE-A peptide SEQ ID NO:44 presented by MEW class I HLA-CW7.

11. The antibody of claim 10,
    wherein the TCR comprises Vα-12.1 domain and Vβ-1 domain that binds to the MAGE-A HLA epitope and
    wherein the TCR Vβ-1 domain is encoded by SEQ ID NO: 2 and the TCR Vα-12.1 is encoded by SEQ ID NO: 1.

12. The antibody of claim 10, wherein the scFv is obtained from OKT3.

13. A method for producing the single polypeptide chain of claim 1, the method comprising:
    culturing a cell comprising a nucleic acid molecule encoding the single polypeptide chain of claim 1 in a culture,
    expressing the single polypeptide chain, and
    separating the single polypeptide chain from the culture.

* * * * *

UNITED STATES PATENT AND TRADEMARK OFFICE
CERTIFICATE OF CORRECTION

PATENT NO. : 11,098,115 B2
APPLICATION NO. : 14/348465
DATED : August 24, 2021
INVENTOR(S) : Ralph Alexander Willemsen and Johan Renes It is certified that error appears in the above-identified patent and that said Letters Patent is hereby corrected as shown below:

In the Specification

| | | |
|---|---|---|
| Column 2, | Line 43, | change "$_n$(SEQ" to --$_n$ (SEQ-- |
| Column 15, | Line 34, | change "heterodimer GPCRs" to --heterodimer form. GPCRs-- |
| Column 16, | Line 27, | change "MUG" to --MUC-- |
| Column 17, | Line 24, | change "CD 117" to --CD117-- |
| Column 17, | Line 52, | change "CD 14" to --CD14-- |
| Column 19, | Line 4, | change "A8. For" to --A8, for-- |
| Column 19, | Line 54, | change "CD44, -v6" to --CD44,-v6-- |
| Column 26, | Line 22, | change "A 1" to --A1-- |

In the Claims

| | | | |
|---|---|---|---|
| Claim 10, | Column 50, | Line 46, | change "MEW" to --MHC-- |
| Claim 10, | Column 50, | Line 48, | change "MEW" to --MHC-- |

Signed and Sealed this
Fifth Day of October, 2021

Drew Hirshfeld
*Performing the Functions and Duties of the
Under Secretary of Commerce for Intellectual Property and
Director of the United States Patent and Trademark Office*